United States Patent [19]
Kim

[11] Patent Number: 5,759,573
[45] Date of Patent: Jun. 2, 1998

[54] CYCLODEXTRIN LIPOSOMES ENCAPSULATING PHARMACOLOGIC COMPOUNDS AND METHODS FOR THEIR USE

[75] Inventor: Sinil Kim, Solana Beach, Calif.

[73] Assignee: DepoTech Corporation, San Diego, Calif.

[21] Appl. No.: 535,256

[22] PCT Filed: Apr. 22, 1994

[86] PCT No.: PCT/US94/04490

§ 371 Date: Dec. 21, 1995

§ 102(e) Date: Dec. 21, 1995

[87] PCT Pub. No.: WO94/23697

PCT Pub. Date: Oct. 27, 1994

[51] Int. Cl.$^6$ .......................... A61K 9/127; A61K 9/133
[52] U.S. Cl. .......................................... 424/450; 436/829
[58] Field of Search .............................. 424/450, 1.21, 424/9.321, 9.51; 428/402.2; 436/829; 514/58

[56] References Cited

U.S. PATENT DOCUMENTS 4,935,407  6/1990  Luider .................................. 514/58
5,236,907  8/1993  Ueno ................................... 514/530

OTHER PUBLICATIONS

Takada BBA 802, 237, 1984.

Osrro Liposomes Marcel Dekker Inc p. 277, 1987.

Manosroi Drug Dev. & Ind. Pharmacy 16(5) p. 37 (1990).

*Primary Examiner*—Gollamudi S. Kishore
*Attorney, Agent, or Firm*—Fish & Richardson P.C.

[57] ABSTRACT

Liposomes containing cyclodextrin in the encapsulated aqueous phase are useful for encapsulation of biologically active substances, especially those which are hydrophilic. The encapsulated cyclodextrin facilitates a slow, controlled release of pharmacologic compounds from the liposomes. The novel methods of the present invention allow the treatment of a variety of pathophysiological states by administering the cyclodextrin-containing liposomes encapsulating the pharmacologic compounds. The present invention also provides a novel method of extending the half life of a pharmacologic compound in an animal.

48 Claims, 6 Drawing Sheets

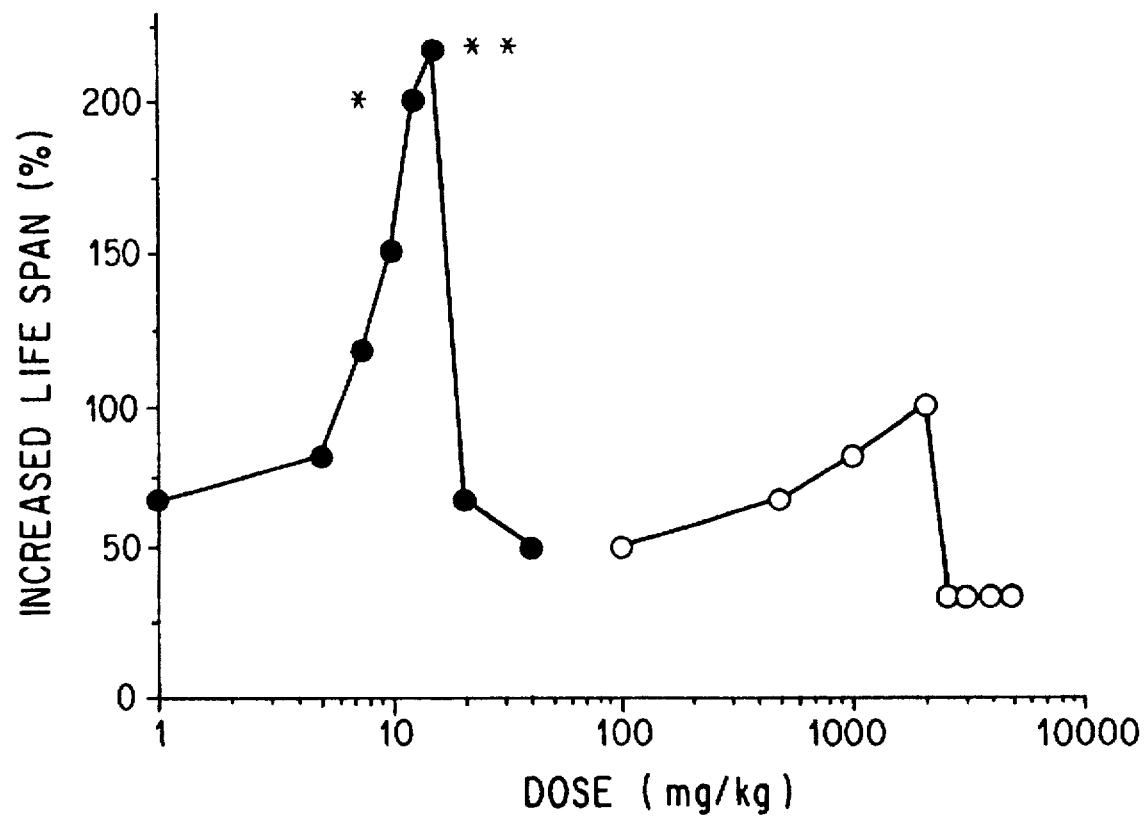
F I G. 11

CYCLODEXTRIN LIPOSOMES ENCAPSULATING PHARMACOLOGIC COMPOUNDS AND METHODS FOR THEIR USE

This application is a 371 of PCT/US94/04,490 filed Apr. 22, 1994 and a Continuation-in-Part application of U.S. Ser. No. 08/051,135, filed Apr. 22, 1993, now abandoned.

BACKGROUND OF THE INVENTION

1. Field of the Invention

The present invention relates generally to the field of liposome technology and pharmacotherapy. More specifically, the present invention relates to novel liposomes encapsulating pharmacologic compounds and cyclodextrins and to methods for their use.

2. Description of the Related Art

Liposomes are artificial lipid or phospholipid vesicles enclosing aqueous internal chambers into which molecules, e.g., drugs, can be encapsulated with the intention of achieving slow release of the drug after administration of the liposome to an individual. In recent years, several types of liposomes have been described (U.S. Pat. No. 4,552,803 to Lenk; U.S. Pat. No. 4,310,506 to Baldeschwieler; U.S. Pat. No. 4,235,871 to Papahadjopoulos; U.S. Pat. No. 4,224,179 to Schneider; U.S. Pat. No. 4,078,052 to Papahadjopoulos; U.S. Pat. No. 4,394,372 to Taylor; U.S. Pat. No. 4,308,166 to Marchetti; U.S. Pat. No. 4,485,054 to Mezei; and U.S. Pat. No. 4,508,703 to Redziniak; Szoka, et al., 1980, *Ann. Rev. Biophys. Bioeng.* 9:465–508; *Liposomes*, Marc J. Ostro, Ed., Marcel-Dekker, Inc., New York, 1983; Poznansky and Juliano, *Pharmacol. Rev.* 36:277–236, 1984: Kim, et al, *Biochim. Biophys. Acta* 728:339–348, 1983; Kim et al., *Biochim. Biophys. Acta* 646:1–10, 1981). Unilamellar liposomes have a single bilayer membrane enclosing an aqueous volume (Huang, 1969, *Biochemistry* 8:334–352) while multilamellar liposomes have numerous concentric membranes (Bangham et al, 1965, *J. Mol. Biol.* 13:238–252). Multivesicular liposomes are different from either unilamellar or multilamellar liposomes in that multivesicular liposomes have multiple non-concentric aqueous chambers (Kim et al., 1983, *Biochim. Biophys. Acta* 728:339–348).

Liposome delivery systems have been proposed for a variety of pharmacologically active compounds including antibiotics, hormones and anti-neoplastic agents (*Liposomes*, 1983, Marc J. Ostro, Ed., Marcel-Dekker, Inc., New York, 1983). The use of liposomes to encapsulate pharmacologic agents and the efficacy of liposomal delivery systems differs according to the water-and lipid-solubility of the drug. For example, hydrophilic substituted for encapsulation in multivesicular liposomes. In contrast, hydrophobic, water insoluble compounds tend to be incorporated into the lipid bilayer. These compounds, therefore, are not well suited for encapsulation into the aqueous internal chambers of a liposome delivery system. The cyclodextrin class of compounds, especially β-cyclodextrin, has been used successfully to solubilize water-insoluble hydrophobic compounds (Strattan, January 1992, *Pharm. Tech.* 68–74; Strattan, February 1992, *Pharm. Tech.* 52–58; Stern, *DN&P*, 2:410–415, 1989; Pagington, *Chem. Brit.* 23:455–458, 1987).

Encapsulation of water-soluble pharmacologic compounds such as methotrexate into a variety of drug delivery systems has been previously reported. However, the release rates of methotrexate were found to be rapid and the previous encapsulations did not result in any major changes in pharmacokinetics. Kimelberg et al. reported the half-life of the liposomal methotrexate preparation in the cerebrospinal fluid to be extremely short (less than 1 hour) and not significantly different from the unencapsulated drug.

Many investigators have attempted to target pharmacologic agents, e.g., antineoplastic drugs such as methotrexate to a tumor with the intention of reducing systemic toxicity and increasing tumor kill. One approach is to instill the drug directly into a tumor-containing cavity such as peritoneal cavity or subarachnoid space. However, such intracavitary therapy is not always successful. One of the problems is that the intracavitary clearance is rapid, resulting in a short drug exposure. For a cell-cycle phase specific drug like methotrexate, prolonged exposure is necessary for optimal efficacy.

The prior art remains deficient in the lack of an effective liposomal delivery system for some water soluble and biologically active compounds that are released too rapidly from liposomes to be practical and useful. The prior art is also deficient in the lack of effective methods for the controlled release of such compounds.

SUMMARY OF THE INVENTION

In one embodiment of the present invention, there is provided a liposome composition, comprising a water soluble compound encapsulated in said liposome, wherein said liposome composition contains encapsulated cyclodextrin.

In another embodiment of the present invention, there is provided a method of treating a pathophysiological state in an individual comprising administering a liposome composition to the individual, said composition comprising a pharmacologically effective amount of a water soluble compound encapsulated in said liposome, wherein said liposome composition contains encapsulated cyclodextrin.

In yet another embodiment of the present invention, there is provided a method of increasing the half-life of a compound in an animal comprising the step of administering an admixture of liposomes encapsulating the compound, wherein said liposome encapsulates cyclodextrin.

Other and further objects, features and advantages will be apparent from the following descriptions of the presently preferred embodiments in the invention which are given for the purpose of disclosure and when taken in conjunction with the accompanying drawings.

DESCRIPTION OF THE PREFERRED EMBODIMENTS

The term "multivesicular liposomes" as used throughout the specification and claims means man-made, microscopic lipid-vesicles consisting of intersecting lipid bilayer membranes, enclosing multiple non-concentric aqueous chambers and characterized by a neutral lipid separating the leaflets of a bilayer membrane. In contrast, unilamellar liposomes have a single aqueous chamber, and multilamellar liposomes have multiple "onion-skin" type of concentric membranes, in between which are shell-like concentric aqueous compartments.

The term "solvent spherule" as used throughout the specification and claims means a microscopic spheroid droplet of organic solvent, within which is multiple smaller droplets of aqueous solution. The solvent spherules are suspended and totally immersed in a second aqueous solution.

The term "MVL-CD-MTX" means a formulation containing methotrexate encapsulated into multivesicular liposomes in the presence of cyclodextrin.

BRIEF DESCRIPTION OF THE DRAWINGS

The drawings are not necessarily to scale. Certain features of the invention may be exaggerated in scale or shown in schematic form in the interest of clarity and conciseness.

FIG. 11 shows the increased life time (ILS) versus dose (mg/kg) of mice treated on day 1 with unencapsulated methotrexate (open circles) and with MVL-CD-MTX (shaded circles). Each data point represents median ILS from a group of five mice. Comparison to optimal unencapsulated methotrexate dose (2000 mg/kg) was by the Mann-Whitney non-parametric test: *, $p<0.02$; **, $p<0.01$.

DETAILED DESCRIPTION OF THE INVENTION

Figure 1:
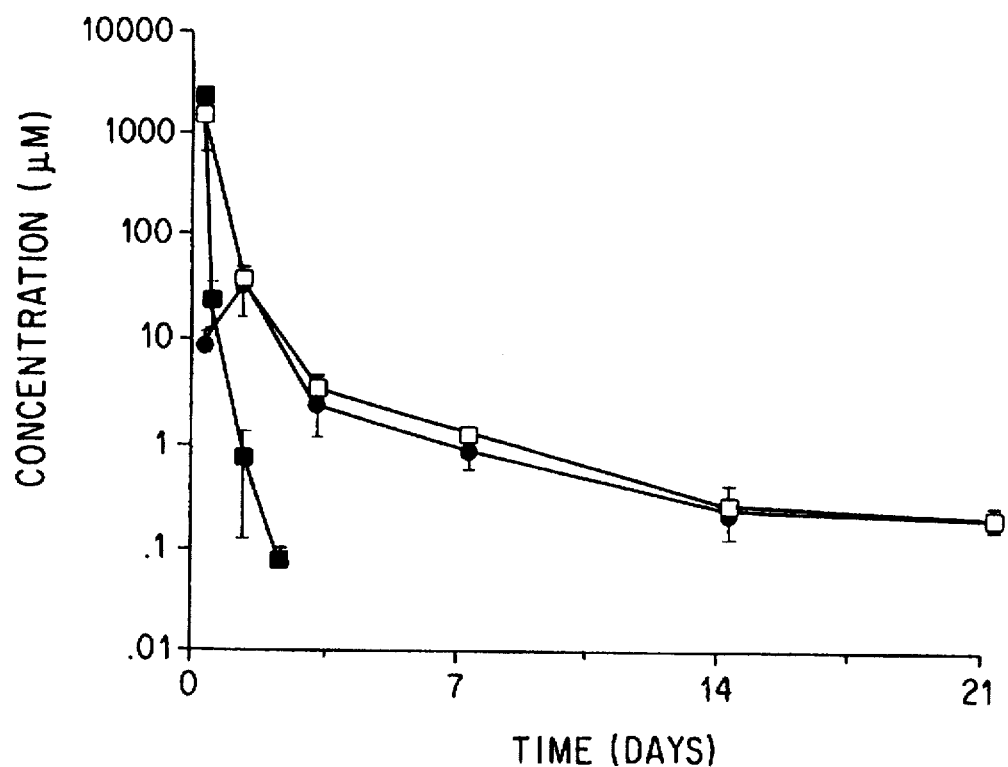
FIG. 1 shows the concentrations of methotrexate in cerebrospinal fluid (CSF) after intracisternal injection of 100 µg (0.22 µmol) of multivesicular liposomes encapsulating methotrexate and cyclodextrin (MVL-CD-MTX) (closed circle, free; open square, total) or as unencapsulated methotrexate (closed square). Each data point represents mean and standard deviation from three rats.

The present invention is directed to forming inclusion complexes of water-soluble compounds, such as methotrexate, with cyclodextrins, preferably β-cyclodextrin, and to encapsulating the inclusion complex into liposomes for controlled release. For use in the practice of this invention the cyclodextrin preferably forms an inclusion complex with the water soluble compound wherein the apolar cavity of the cyclodextrin is occupied by or sequesters the compound sufficiently to slow the rate of release from the liposome composition. The rim or the periphery of the inclusion complex is hydrophilic with the result that the inclusion complex forms a solution in aqueous media. The cyclodextrin-complexed water soluble substance can then be encapsulated into liposomes.

In addition to preventing incorporation of water soluble compounds into the lipid layers of the liposomes during their formation, Applicants have discovered that formation of an inclusion complex results in a reduction in the rate of release of the hydrophilic compound from the liposome compared to the rate of release of the same compound encapsulated in the absence of the cyclodextrin.

The present invention provides a liposome composition, comprising a pharmacologically active amount of a biologically active compound encapsulated in said liposome, wherein said liposome composition further contains encapsulated cyclodextrin. Preferably, the biologically active compound is water soluble. In the practice of this invention, the water soluble compound generally has water solubility of greater than about 1 µg/ml, preferably greater than about 100 µg/ml, and most preferably greater than about 1 mg/ml, in the absence of cyclodextrin.

As used herein, the term "pharmacologic" or "pharmacologically active" is used interchangeably with "biological" or "biologically active".

Cyclodextrins are chiral, toroidal-shaped molecules formed by the action of the enzyme cyclodextrin transglycosylase on starch. These cyclic oligomers contain from 6 to 12 glucose units bonded through α-(1,4)-linkages. The three smallest homologs, α-cyclodextrin, β-cyclodextrin and γ-cyclodextrin are available commercially; larger homologs must be produced and isolated individually. The secondary 2- and 3-hydroxy groups line the mouth of the cyclodextrin cavity and have a staggered orientation. The primary 6-hydroxyls are at the opposite end of the molecule. The inside of the cyclodextrin cavity is relatively hydrophobic since all hydroxyls are directed toward the outside of the molecule.

It is specifically contemplated that many different types of cyclodextrins would be useful in the compositions and methods of the present invention. For example, the present invention may use natural α-, β- or γ cyclodextrins. Similarly, the present invention may utilize semisynthetic substituted cyclodextrins such as; methyl cyclodextrins, ethyl cyclodextrins, hydroxyethyl cyclodextrins, hydroxypropyl cyclodextrins, branched cyclodextrins, cyclodextrin polymers or monosuccinyl dimethyl β-cyclodextrin. Most preferred for the compositions and methods of the present invention is 2-hydroxypropyl-β-cyclodextrin.

Generally, the concentration of cyclodextrin used in preparing the liposomes of the present invention is that which slows the release of a pharmacologic compound from the liposome after administration to an animal. Preferably, the cyclodextrin is present in the liposome composition in an amount of from about 10 milligrams per ml to about 400 milligrams per ml. More preferably, the amount of cyclodextrin in the liposome is about 100 mg/ml.

Generally, the liposome of the present invention may be any that when prepared with encapsulated cyclodextrin provides slow, controlled release of pharmacologic compounds. Preferably, the liposome is selected from the group of unilamellar, multilamellar and multivesicular liposomes. Most preferably, the liposome is a multivesicular liposome.

Generally, the biologically active compound encapsulated in the liposome oil the present invention may be any whose release rate from a liposome encapsulating cyclodextrin is slower than that in the absence of the cyclodextrin. Therapeutic biologically active compounds may be selected from the general group consisting of anti-neoplastic agents, anti-infective agents, anti-depressives, antiviral agents, anti-nociceptive agents, anxiolytics and hormones.

Representative examples of anti-neoplastic agents useful in the compositions and methods of the present invention include methotrexate, taxol, tumor necrosis factor, chlorambucil, interleukins, bleomycin, etoposide, fluorouracil and vinblastine.

Representative examples of anti-infective agents useful in the compositions and methods of the present invention include pentamidine, metronidazole, penicillin, cephalexin, tetracycline and chloramphenicol.

Representative examples of anti-viral agents useful in the compositions and methods of the present invention include dideoxyoytidine, zidovudine, acyclovir, interferons, dideoxyinosine and ganciclovir.

Representative examples of anxiolytics and sedatives useful in the compositions and methods of the present invention include benzodiazepines such as diazepam, barbiturates such as phenobarbital and other compounds such As buspirone and haloperidol.

Representative examples of hormones useful in the compositions and methods of the present invention include estradiol, prednisone, insulin, growth hormone, erythropoietin, and prostaglandins.

Representative examples of anti-depressives useful in the compositions and methods of the present invention include fluoxetine, trazodone, imipramine, and doxepin.

Representative examples of anti-nociceptives useful in the compositions and methods of the present invention include hydromorphine, oxycodone, fentanyl, morphine and meperidine.

The list of therapeutic biologically active agents described above is only exemplary and not meant to limit the scope of the present invention in any fashion. Many other classes of pharmacologic agents would be useful in the compositions and methods of the present invention, including local anesthetics, vitamins, vaccines, wound healing stimulators, immunosuppressives, anti-emetics, anti-malarial agents, anti-fungal agents, anti-psychotics, anti-pyretics, coagulants, diuretics, calcium channel blockers, bronchodilatory agents, etc.

The present invention also provides a method of increasing the half-life of a pharmacologic compound in an animal comprising the step of administering an admixture of liposomes encapsulating the pharmacologic compound, wherein said liposome further encapsulates cyclodextrin.

The present invention additionally provides a method of treating a pathophysiological state in an individual comprising administering a liposome composition to the individual, said composition comprising a therapeutically effective amount of a compound encapsulated in said liposome, wherein said liposome composition further encapsulates cyclodextrin. The term "therapeutically effective" as it pertains to the compositions of the invention means that biologically active therapeutic agent is present in the aqueous phase within the vesicles at a concentration sufficient to achieve a particular medical effect for which the therapeutic agent is intended. Examples, without limitation, of desirable medical effects that can be attained are chemotherapy, antibiotic therapy, and regulation of metabolism. Exact dosages will vary depending upon such factors as the particular therapeutic agent and desirable medical effect, as well as patient factors such as age, sex, general condition, and the like. Those of skill in the art can readily take these factors into account and use them to establish effective therapeutic concentrations without resort to undue experimentation.

Generally, however, the dosage range appropriate for human use includes the range of 0.1–6000 mg/sq m of body surface area. For some applications, such as subcutaneous administration, the dose required may be quite small, but for other applications, such as intraperitoneal administration, the dose desired to be used may be very large. While doses outside the foregoing dose range may be given, this range encompasses the breadth of use for practically all the biologically active substances.

The liposomes of the present invention may be administered by any desired route. For example, administration may be intrathecal, intraperitoneal, subcutaneous, intramuscular, intravenous, intralymphatic, oral and submucosal. Administration may also be to different kinds of epithelia including the bronchiolar epithelia, the gastrointestinal epithelia, the urogenital epithelia and various mucous membranes in the body. As one skilled in the art will appreciate, the best route of administration may depend upon the biologically active compound selected. For instance, although methotrexate can be given orally, parenteral administration has certain advantages. The absorption rate of methotrexate after oral administration is highly variable among patients and appears to be saturable. In contrast, absorption of the drug after im or sc administration is much more predictable and complete, resulting in higher serum concentrations than after an oral dose.

Cyclodextrin-containing liposomes are useful in extended-release drug delivery of subcutaneously administered pharmacological agents for several reasons. They are quite stable in storage. Moreover, the drug can be released over extended time periods, both in vitro and in vivo. Their sponge-like internal structure, results in efficient encapsulation into a chambers, stability in storage, and extended release in vivo. For instance, the half-life in plasma of methotrexate can be increased by 206-fold over that of free methotrexate, and with peak plasma concentration was 126-fold lower compared to unencapsulated methotrexate. As a consequence of the significant modifications of the pharmacokinetics achieved by encapsulation of a drug encapsulated in the liposome in the presence of cyclodextrin, drug potency can be increased by over 100 fold. For instance the potency of methotrexate can be increased by 130 fold through administration in accordance with the teachings of this invention, and $LD_{50}$ can be decreased 110 fold. These changes in potency and $LD_{50}$ indicate no significant change in therapeutic index due to introduction into the liposomes during encapsulation of the biologically active compound.

The liposomal compositions of the present invention may be modified to impart organ or cellular targeting specificity. These modifications may be particularly relevant when using the liposomal compositions of the present invention to administer pharmacologic agents that are highly toxic or that produce severe side effects.

The targeting of liposomes has been classified based on anatomical and mechanistic factors. Anatomical classification is based on the level of selectivity, e.g., organ-specific, cell-specific or organelle-specific. Mechanistic targeting can be distinguished based upon whether it is passive or active. Passive targeting utilizes the natural tendency of liposomes to distribute to cells of the reticulo-endothelial system in organs which contain sinusoidal capillaries. Active targeting, in contrast, involves alteration of the liposome by coupling the liposome to a specific ligand such as a monoclonal antibody, sugar, glycolipid, protein or by changing the composition or size of the liposome in order to achieve targeting to organs and cell types other than the naturally occurring sites of localization. See, e.g., *Remington's Pharmaceutical Sciences*, Gannaro, A. R., ed., Mack Publishing, 18th edition, pp. 1691-1693. For instance, MVL-CD-MTX particles can be synthesized in large average sizes to decrease their uptake into lymphatics and systemic circulation after injection into body cavities or into tissue spaces, such as subcutaneous space. Their large size may also inhibit uptake into macrophages.

The surface of the targeted delivery system may be modified in a variety of ways. In the case of a liposomal composition of the present invention, lipid groups may be incorporated into the lipid bilayer of the liposome in order to maintain the targeting ligand in stable association with the liposomal bilayer. Various linking groups can be used for joining the lipid chains to the targeting ligand. The compounds bound to the surface of the targeted delivery system may vary from small haptens of from about 125-200 molecular weight to much larger antigens with molecular weights of at least 6000, but generally of less than 1 million molecular weight. The following examples are given for the purpose of illustrating various embodiments of the methods of the present invention and are not meant to limit the present invention in any fashion.

EXAMPLE 1

Synthesis of Multivesicular Liposome-Methotrexate-βCyclodextrin Formulation, MVL-CD-MTX Multivesicular liposomes encapusulating methotrexate in the presence of cyclodextrin (MVL-CD-MTX) were prepared using a method described by Kim et al (*Cancer Treat. Rep.* 71:705, 1987) with some modifications. Briefly, for each batch of MVL-CD-MTX, the discontinuous aqueous phase consisted of 2-hydroxypropyl-β-cyclodextrin solution (100 mg/ml), HCl (0.1N) and methotrexate (10 mg/ml). One ml of the discontinuous aqueous phase was added into a one dram vial containing 13.9 μmol dioleoyl lecithin, 3.15 μmol dipalmitoyl phosphalidy/glycerol, 22.5 μmol cholesterol, 2.7 μmol triolein and 1 ml chloroform. The vial was attached horizontally to the head of a vortex mixer and shaken at maximum speed for 6 minutes. One-half of the resulting "water-in-oil" emulsion was expelled rapidly through a narrow-tip Pasteur pipette into each of two 1-dram vials, each containing 2.5 ml water, glucose (32 mg/ml) and free-base lysine (40 μM). Each vial was then shaken on the vortex mixer for 5 seconds at maximum speed to form chloroform spherules. The chloroform spherrule suspensions in the two vials were transferred into a 250-ml Erlenmeyer flask containing 5 ml water, glucose (32 mg/ml), and free base lysine (40 mM). A stream of nitrogen gas at 7 liter per minute was used to evaporate the chloroform over a 10-15 minute period a 37° C. The MVL-CD-MTX particles were then isolated by centrifugation at 600×g for 5 minutes and washed three times with 0.9% NaCl solution.

EXAMPLE 2

Intrathecal pharmacokinetic studies

Rats were anesthetized with ketamine HCl (90 mg/kg and acetopromazine maleate (2.2 mg/kg, injected intramuscularly) and mounted in a conventional stereotaxic frame. Using a No. 15 blade, a midline cutaneous incision approximately 1 cm in length was made from the occipital crest to just behind the ears. The muscle ligament along the occipital crest at the skull was detached with a scalpel for 4 mm on either side of the midline. Using both the sharp and blunt ends of a periosteal elevator, the muscle from the occipital bone was freed down to the atlanto-occipital membrane. A retractor was placed in the incision to draw the muscle aside and obtain a clear view of the atlanto-occipital membrane. Either 20 μl unencapsulated methotrexate or 20 μl MVL-CD-MTX in 0.9% NaCl, both containing 100 μg (0.22 μmol) methotrexate, was then injected over 20 seconds via a 30-gauge needle through the membrane. The needle was withdrawn, the skin was sutured with 3-0 silk, and the animal was given 10 ml lactated Ringer'solution subcutaneously for hydration.

At appropriate time points after injection, the atlanto-occipital membrane was again exposed under anesthesia and a sample of cerebrospinal fluid ranging from 30 to 60 μl was obtained through a 19-gauge needle. Cerebrospinal fluid samples were obtained from three rats at each time: at 1 minutes and at 4, 24, and 48 hours after injection in the unencapsulated methotrexate group and at 1 minutes and at 1, 3, 7, 14 and 21 days after injection in the Depo-methotrexate group. The CSF samples from the MVL-CD-MTX group were diluted with 70 μl 0.9% NaCl solution and then immediately centrifuged in an Eppendorf Microfuge for 1 minute to separate a supernatant containing released free methotrexate from a pellet containing encapsulated methotrexate. Next, 50 μl of methanol and 50 μl of sterile water were sequentially added to the pellet and vortexed to break the MVL-CD-MTX particles. The cerebrospinal fluid samples were then kept frozen at −20° C. until analyzed using a high-performance liquid chromatography (HPLC) system as described below.

After cerebrospinal fluid sampling, the animals were sacrificed with an overdose of ketamine (90 mg/kg) and acetopromazine (20 mg/kg), injected intraperitoneally. Blood samples were obtained via cardiac puncture and thorough exsanguination was performed. The plasma was separated and kept frozen at −20° C. until analyzed by Emit methotrexate assay on COBAS Fara instrument (Roche Diagnostic Systems). The calvarium was then exposed and carefully removed with a bone rongeur. The entire content of the cranial compartment was collected by scooping out the exposed brain with a spatula and washing the cranial vault thoroughly with distilled water. The spinal compartment content was then collected separately; the spinal cord was extruded forward into the cranial vault by pushing distilled water rapidly through a 19-gauge needle inserted into the lower lumbar spinal canal at a point 2.5 cm rostral to the origin of the tail. The empty spinal canal was washed out thoroughly with distilled water to complete collection of methotrexate in the spinal canal. The cranial compartment samples were analyzed separately from the spinal canal samples. Both tissue samples were homogenized with water using a Polytron homogenizer.

EXAMPLE 3

Measurement of methotrexate

The amount of methotrexate in the spinal compartment was calculated by adding the amount from the cisternal cerebrospinal fluid sample. The homogenized samples of brain or spinal cord were analyzed with HPLC after extraction as described by Alkayal et al. *Ther. Drug Monit.* 12:191 (1990). Briefly, in a glass centrifuge tube, a 500 µl aliquot of homogenate, 100 µl of theophylline aqueous solution (internal standard, 2.0 mg/ml), 250 µl trichloroacetic acid solution (10% in water), and 250 µl glacial acetic acid were placed and mixed. Then, methotrexate free acid was extracted with 5 ml ethyl acetate. Ethyl acetate organic phase was decanted and evaporated under nitrogen at 60° C. The extracted residue was dissolved in 200 µl of mobile phase and 100 µl of the resulting solution was injected into the HPLC. Mobile phase consisting of $H_3PO_4$ (10 mM): methanol in 180:540:280 ratio (final pH of 3) was pumped at a flow rate of 1 ml/min with a Waters model 510 pump through a Beckman ultrasphere ODS 5 µm×4.6 mm×25 cm column (Beckman, Carlsbad, Calif.). Methotrexate was detected at 303 nm with a Waters Model 490 programmable multiwavelength detector (Waters Assoc., Milford, Mass.). The retention times of theophylline and methotrexate were 5.2 minutes and 7.2 minutes, respectively. The limit of detection was 5 pmol of methotrexate injected.

EXAMPLE 4

Pharmacokinetic analysis

The RSTRIP computer program (MicroMath Scientific Software, Salt Lake City, Utah) was used to perform the pharmacokinetics analysis. The area under the curve (AUC) was determined by linear trapezoidal rule up to the last measured concentration and extrapolated to infinity.

EXAMPLE 5

Characterization of MVL-CD-MTX

The average volume-weighted diameter of MVL-CD-MTX was found to be 14.1±3.4 (±standard deviation, SD). Encapsulation efficiency was 64.5±6% (n=6) and captured volume was 12.9±1.0 µl/umol of lipids. Storage of MVL-CD-MTX at 4° C. in 0.9% NaCl solution resulted in less than 5% release of methotrexate after 4 months.

EXAMPLE 6

CNS Pharmacokinetics

Figure 2:
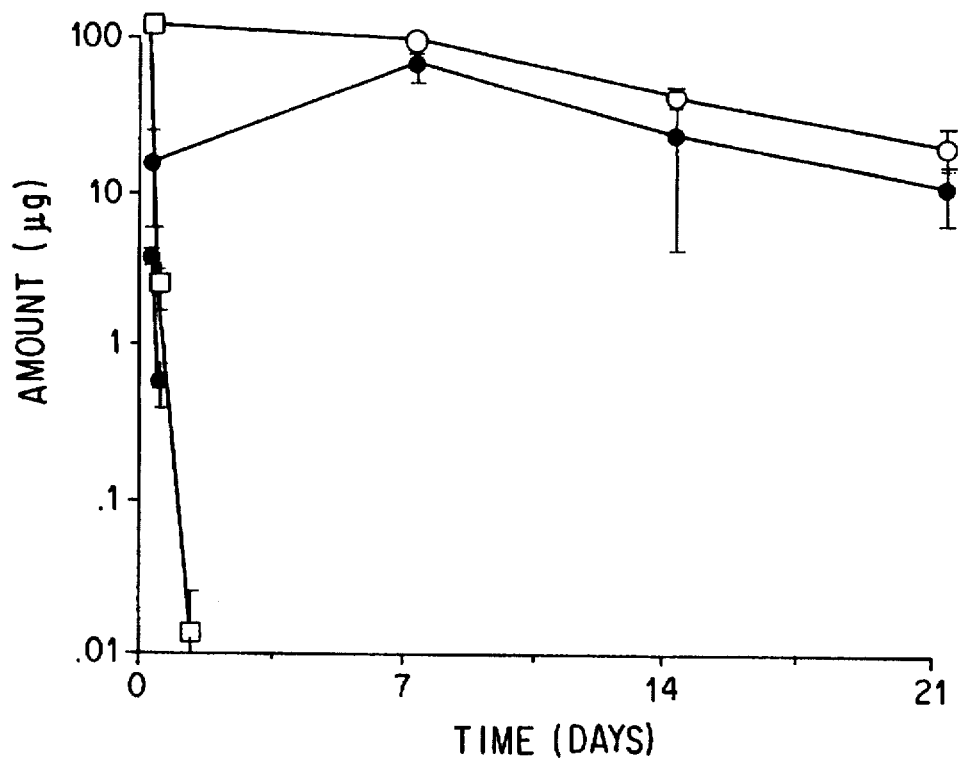
FIG. 2 shows the amount of methotrexate remaining within the central nervous system (CNS) after intracisternal injection of 100 µg methotrexate as MVL-CD-MTX (open circle, total within CNS; closed circle, within cranial compartment) or as unencapsulated methotrexate (open square, total; closed square, cranial). Each data point represents mean and standard deviation from three rats.

FIGS. 1 and 2 compare the central nervous system (CNS) pharmacokinetics (in terms of CSF concentration and CNS amount) for MVL-CD-MTX and unencapsulated methotrexate. The CSF concentration of free methotrexate reached a maximum on day 1 and then decreased in a biexponential fashion with initial and terminal half-lives of 0.41 and 5.4 days, respectively. The terminal half-life was 18 times longer than that for unencapsulated methotrexate.

Following injection of MVL-CD-MTX, the total amounts of drug within CNS decreased with a half-life of 9 days compared to 0.03 days for unencapsulated methotrexate. At the end of the 21-day period, 18% of the methotrexate remained within the CNS after MVL-CD-MTX injection.

Pharmacokinetic parameters for methotrexate and MVL-CD-MTX within the CNS are summarized in Table 1. Maximum concentration of free methotrexate after MVL-CD-MTX administration was about 70 times lower than that after administration of unencapsulated methotrexate. The proportion of the total amount of methotrexate within the cranial compartment were 12±8%, 65±11%, 51±40%, and 65±36%, respectively at 1 minute and 7, 14 and 21 days after injection of MVL-CD-MTX and 4±1% and 23±1%, respectively, at 1 minute and 4 hours after injection of unencapsulated methotrexate.

TABLE 1

Pharmacokinetics parameters of methotrexate in the CNS after a 100 µg injection

| | Unencapsulated | MVL-CD-MTX | |
|---|---|---|---|
| | Methotrexate | Free | Total |
| $C_{max}$ (µM) | 1751 ± 302 | 23.7 ± 11.7 | 1133 ± 631 |
| Conc. $t_{1/2}\alpha$ (days) | 0.024 | 0.41 | 0.18 |
| Conc. $t_{1/2}\beta$ (days) | 0.30 | 5.4 | 4.0 |
| AUC (µM × days) | 154.3 | 50.5 | 624.2 |
| Amount $t_{1/2}$ (days) | 0.03 | NA | 9.0 |

$C_{max}$, maximum CSF concentration;
$t_{1/2}$, half-life;
AUC, area under the curve;
NA, not applicable Analysis of plasma concentrations showed undetectable levels of methotrexate (limits of detection being 0.02 µM) except at one time point after unencapsulated drug (4 hours after intracisternal injection: 0.11±0.02 µM).

EXAMPLE 7

Toxicities

No abnormalities were observed in the behavior of rats given injections of MVL-CD-MTX. Three rats injected with MVL-CD-MTX gained weight from 343±5 to 383±19 grams over the 3 weeks. In contrast, control rats without any injections or surgical interventions grew from 340±1 to 400±12 grams.

The encapsulation of methotrexate in multivesicular liposomes resulted in a 18-fold increase in the terminal half-life of free methotrexate from the cerebrospinal fluid. The free methotrexate concentrations stayed above 0.5 µM, considered the minimal cytotoxic concentration estimated from studies in vitro, for 7–14 days after a single injection of MVL-CD-MTX. In contrast, the duration was about 1 day for the unencapsulated drug.

The area under the curve of free concentrations for the MVL-CD-MTX group was one third of that for the unencapsulated group. This may be attributable to saturation of the methotrexate cerebrospinal fluid clearance mechanism when high free methotrexate concentrations occur in the unencapsulated group. A second possibility is that a higher fraction of the free methotrexate penetrates into the brain and spinal cord parenchyma by extended exposure and thus a smaller fraction remains in the cerebrospinal fluid. Yet another possibility is that the area under the curve for the MVL-CD-MTX was underestimated due to the sampling schedule.

The comparison of the total amount of methotrexate and the amount within the cranial compartment (FIG. 2) showed good distribution of MVL-CD-MTX into both spinal and cranial compartments after intracisternal injection. For example, at day 21 the amount of methotrexate within the cranial compartment was only 65±36% of the total (cranial plus spinal) amount. However, a large fraction of methotrexate in the cisternal sample was in the form of free drug after the first day of injection with MVL-CD-MTX. A high density of MVL-CD-MTX particles relative to the cerebrospinal fluid may result in settling of MVL-CD-MTX particles by gravity away from the cisternal cerebrospinal fluid, whereas the released free methotrexate is free to diffuse. The extended release of methotrexate from MVL-CD-MTX, both in vitro and in vivo, indicates that multivesicular liposomes would be useful as a drug depot for methotrexate.

With MVL-CD-MTX, neurotoxicity can be reduced by keeping most of the initial bolus of methotrexate within the multivesicular liposomes and yet tumor kill enhanced by maintaining the free methotrexate to just above the minimum cytotoxic concentration for an extended period. The present invention demonstrates the utility of cyclodextrin liposomes as a slow-releasing drug delivery system for biologically active substances, such as methotrexate. The present invention demonstrates the utility of less frequent intra-CSF administration for the prophylaxis and treatment of leptomeningeal leukemia or carcinomatosis in humans.

EXAMPLE 8

Subcutaneous Administration of MVL-CD-MTX

BDF1 and DBA/2J mice were from Simonsen Laboratories, Gilroy, Calif. The L1210 leukemia was maintained by serial intraperitoneal passage in DBA/2J female mice. MVL-CD-MTX was prepared as described in Example 1.

Subcutaneous (sc) pharmacokinetic studies were done using male BDF1 mice, weighing 20–25 grams. Mice were injected sc into the center of abdominal skin with 10 mg/kg (22 μmoles/Kg) of unencapsulated standard methotrexate or MVL-CD-MTX in 200 μl of 0.9% NaCl solution, using a 30-gauge hypodermic needle. Blood samples were obtained from the jugular vein under anesthesia at time points, 0, 0.25, 1 and 4 hours for the encapsulated methotrexate group and at time points 0, 1, 3, 7, 14 and 21 days for the MVL-CD-MTX group. At each time point, 3 animals were sacrificed. The plasma was separated and kept frozen at −20° C. until analyzed by Emit$^R$ methotrexate assay on COBAS Fara instrument (Roche Diagnostic Systems, Montclair, N.J.).

A full thickness of the abdominal wall tissue, including the entire skin and the underlying peritoneal membrane, was then excised from the costal margin to the inguinal area and from one flank to the other. The entire tissue specimen was homogenized after addition of at least 20 ml of distilled water with a Polytron homogenizer. The homogenate was sonicated for 60 seconds at a maximum setting with a Biosonic IV probe sonicator and filtered through a YMT ultrafiltration membrane (Amicon Corp, product #4104). All the samples were kept at −20° C. until assayed by HPLC.

The RSTRIP program was used to perform the curve fitting. AUC was determined by linear trapezoidal rule up to the last measured concentration and extrapolated to infinity.

EXAMPLE 9

HPLC assay

A mobile phase consisting of $H_3PO_4$ (10 mM): $KH_2PO_4$ (10 mM): methanol at 162:488:350 ratio (pH =3) was pumped at a flow rate of 1 ml/min with a Waters Model 510 pump through a Beckman ultrasphere ODS 5 μl 4.6 mm×25 cm column. Methotrexate was detected at 303 nm by a UV Waters 490 programmable Multiwave-length Detector. Retention time of methotrexate was 5 minutes and the detection limit was 5 pmols injected.

EXAMPLE 10

Toxity and efficacy studies

BDF1 mice were injected with $10^6$ L1210 cells into the peritoneal cavity on Day 0 and treated sc with a single dose of encapsulated methotrecate oar MVL-CD-MTX suspended in 0.9 % NaCl on Day 1. Five animals were in each group except for the control (given 0.9% NaCl alone), where 10 animals were used. Each animal was observed for survival. Median survival time was used to calculate the "increased life span" (ILS) according to the formula:

$$ILS=(T/C)/C \times 100\%$$

where T is the median survival time of treated groups and C is the median survival time for control groups.

EXAMPLE 11

MVL-CD-MTX Pharmacokinetics

Figure 3:
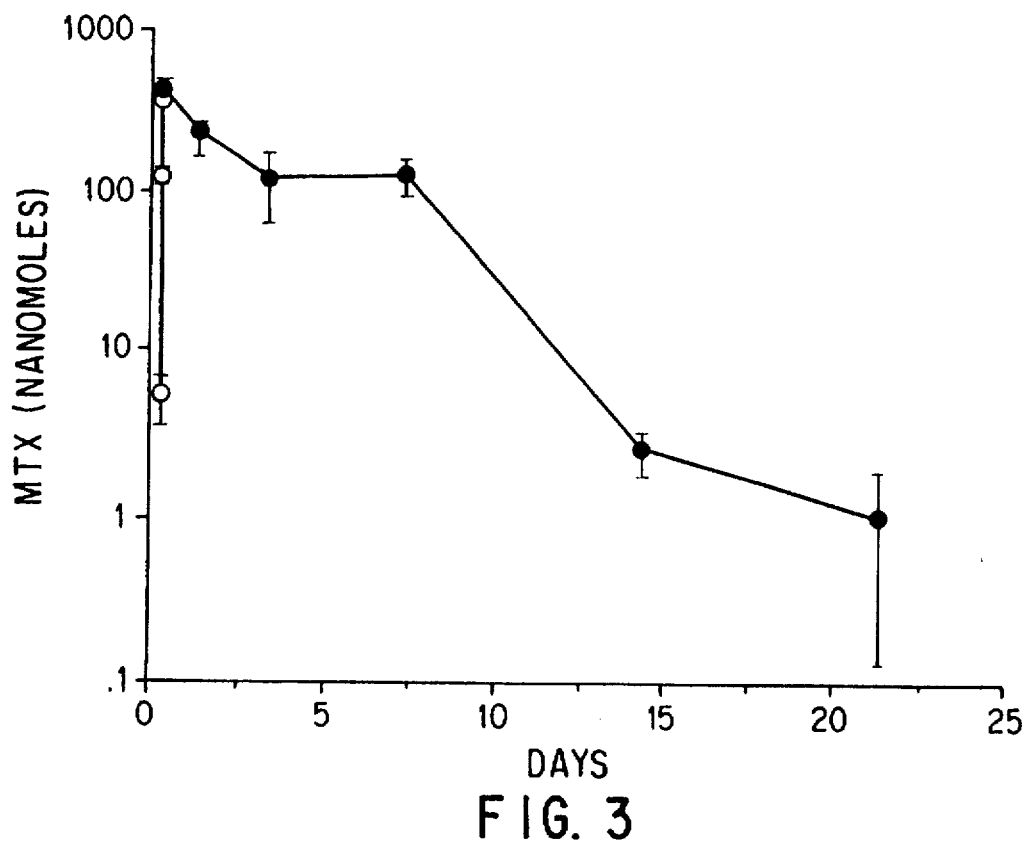
FIG. 3 shows the amount of the unencapsulated methotrexate (open circles) and methotrexate MVL-CD-MTX (closed circles) recovered from the subcutaneous injection site.
Figure 4:
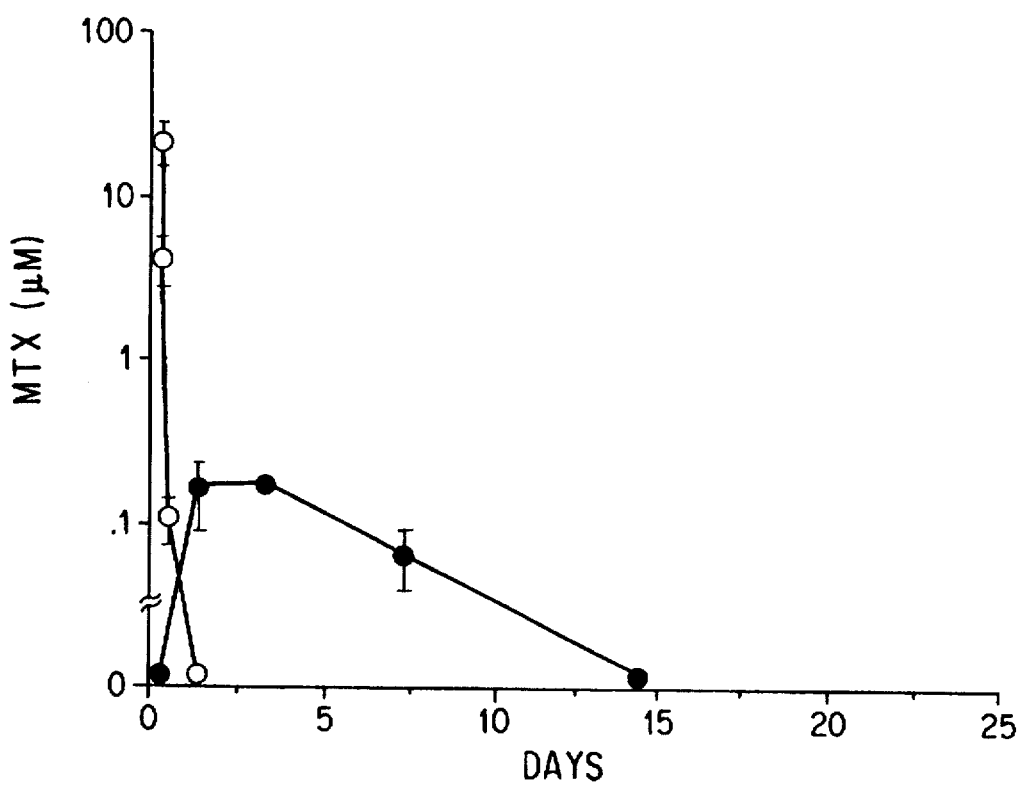
FIG. 4 shows the plasma concentrations of methotrexate following subcutaneous injection of unencapsulated methotrexate (open circles) and MVL-CD-MTX (closed circles).

Pharmacokinetic parameters are summarized in Table 2. After a subcutaneous injection, total amount of methotrexate in skin decreased exponentially with a half-life of 0.16 hours for unencapsulated methotrexate and 50.4 hours for MVL-CD-MTX (FIG. 3). In plasma, the half-lives were 0.53 hours for encapsulated methotrexate and 109 hours for MVL-CD-MTX. Peak plasma levels were 17.4±5.2 μM (SD) at 15 minutes for the encapsulated methotrecate and 0.138±0.061 μM (SD) at day 3 for MVL-CD-MTX (FIG. 4).

TABLE 2

| Pharmacokinetics Parameters | | |
|---|---|---|
| | SUBCUTANEOUS | |
| Amount $t_{1/2}$* (h) | 0.16 | 50.4 |
| | PLASMA | |
| $C_{max}$ ± SD (μM) | 17.4 ± 5.2 | 0.138 ± 0.061 |
| Conc. $t_{1/2}$(h) | 0.53 | 109 |
| AUC (μM × h) | 17.3 | 24.5 |

EXAMPLE 12

Efficacy Of SC MVL-CD-MTX

Figure 5:
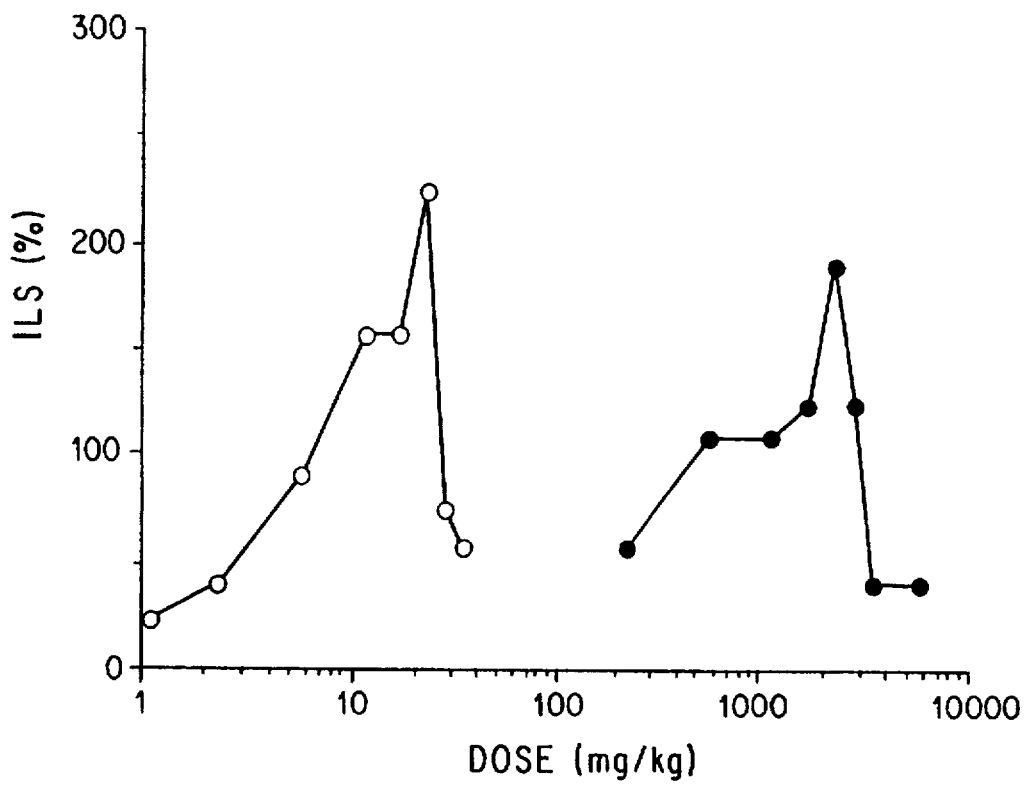
FIG. 5 shows the per cent Increased Life Span (ILS) as a function of the log of the administered dose for unencapsulated methotrexate (open circles) and for MVL-CD-MTX (closed circles).

FIG. 5 shows the ILS curves in a murine L1210 model. The maximum efficacy (ILS max) was 183% for unencapsulated methotrexate and 217% for MVL-CD-MTX (=0.5 by Mann-Whitney U-Test). The relative potency of the single-dose MVL-CD-MTX versus unencapsulated methotrexate was 130 (by PHARM/PCS program, MicroComputer Specialists, Philadelphia, Pa.). The $LD_{50}$ was calculated after probit transformation. The $LD_{50}$ for a single dose of unencapsulated methotrexate was 2650 mg/kg and that for MVL-CD-MTX was 24 mg/kg, a ratio of 110.

The half-life in plasma was 206-fold longer and peak plasma concentration was 126-fold lower compared to unencapsulated methotrexate, whereas the area under the curve was essentially unchanged. As a consequence of the significant modifications of tie pharmacokinetics, drug potency was increased 130 fold and the value of the $LD_{50}$ indicated no significant change in therapeutic index.

EXAMPLE 13

Pharmacokinetics of Peritoneal Cavity Administration In Vitro Drug Release Studies Methotrexate release studies were done by adding a minimum of 40×volumes of 0.9% NaCl solution or human plasma from blood bank to washed MVL-CD-MTX pellets and kept at 4° C. or 37° C. For 37° C. incubation, 0.01% sodium azide was added to inhibit growth of microorganisms. At appropriate time points, aliquots were removed after thorough mixing, diluted with 5-fold volume of 0.9% NaCl solution and centrifuged in an Eppendorf microfuge for 1 minute. After the supernatant was removed, 200 µl of methanol was added to the pellet to break MVL-CD-MTX particles, and the resulting mixture was stored at −20° C. until analysis. The amount of methotrexate in the pellet was analyzed by HPLC and was expressed as percent of the initial amount remaining as MVL-CD-MTX. Methotrexate was measured by HPLC as described in Example 9.

EXAMPLE 14

Pharmacokinetic studies

The in vivo studies were done on male BDF1 mice weighing 18–25 g. The group of mice was injected ip with 10 mg/kg of methotrexate in 1 ml of 0.9% NaCl as unencapsulated methotrexate control, cyclodextrin-methotrexate control (methotrexate 20 mg/ml; 2-hydroxypropyll -β-cyclodextrin, 2 mg/ml; glucose, 6.4 mg/ml; free-base lysine, 8 mM; and HCl, 2 mM) or MVL-CD-MTX. Three mice were sacrificed and blood samples were collected from the jugular vein and placed in a heparinized tube at 0 hour (immediately after the injection), 1 hour and 4 hours after injection of the unencapsulated methotrexate or cyclodextrin-methotrexate complex; and 1, 5, 10 and 20 days after injection of MVL-CD-MTX. The plasma was separated and was kept frozen at −20° C. until analyzed by the Emit[R] methotrexate assay on COBAS Fara Instrument. The Emit[R] assay is a homogeneous enzyme immunoassay technique based on the competition between drug present in the sample and drug labeled with the enzyme glucose-6-phosphate dehydrogenase for antibody binding sites. The limit of sensitivity was 0.02 µM.

Five µl of the peritoneal fluid samples were collected into a glass capillary pipette and diluted into 140 µl of 0.9% NaCl solution. For the animals injected with MVL-CD-MTX, the samples were spun in Eppendorf microfuge for 1 minute to separate the supernatant (free methotrexate) and pellet (encapsulated methotrexate). Fifty µl of methanol was added to the pellet and vortexed to break multivesicular particles. The peritoneal cavities were then washed out thoroughly with 2–3 ml of 0.9% NaCl solution thrice. All samples were kept frozen at −20° C. until assayed by HPLC. Extraction of the samples was not necessary, no internal standard was used and there were no interfering peaks. RSTRIP computer program was used to analyze pharmacokinetic data. The area under the curve was determined by linear trapezoidal rule up to the last measured concentration and extrapolated to infinity.

EXAMPLE 15

Efficacy and toxicity studies

BDF1 mice were inoculated ip with $10^6$ L1210 cells on Day 0, and treated on Day 1 with a single ip injection of unencapsulated methotrexate, MVL-CD-MTX, or blank multivesicular liposomes in 1 ml of 0.9NaCl solution. There were five mice per group and fifteen mice were used as untreated controls (given 1 ml of 0.9% NaCl solution). The result was expressed as "increased life span".

EXAMPLE 16

In vitro release studies

The resulting multivesicular liposome particles had a volume-weighted average diameter (±SD) of 11.3±3.3 µM (FIG. 6 and 7) and the percentage of capture of 64.5±6.0 % (n=6). Storage of MVL-CD-MTX in 0.9% NaCl solution at 4° C. resulted in less than 5% leakage at 4 months. At 37° C. in 0.9% NaCl solution, there was 63±12% (means±SD) of the initial amount of methotrexate inside the multivesicular liposome particles after 3.5 months. In human plasma at 37° C., the half-life of drug release was 40 days (FIG. 8).

EXAMPLE 17

Pharmacokinetics

Figure 8:
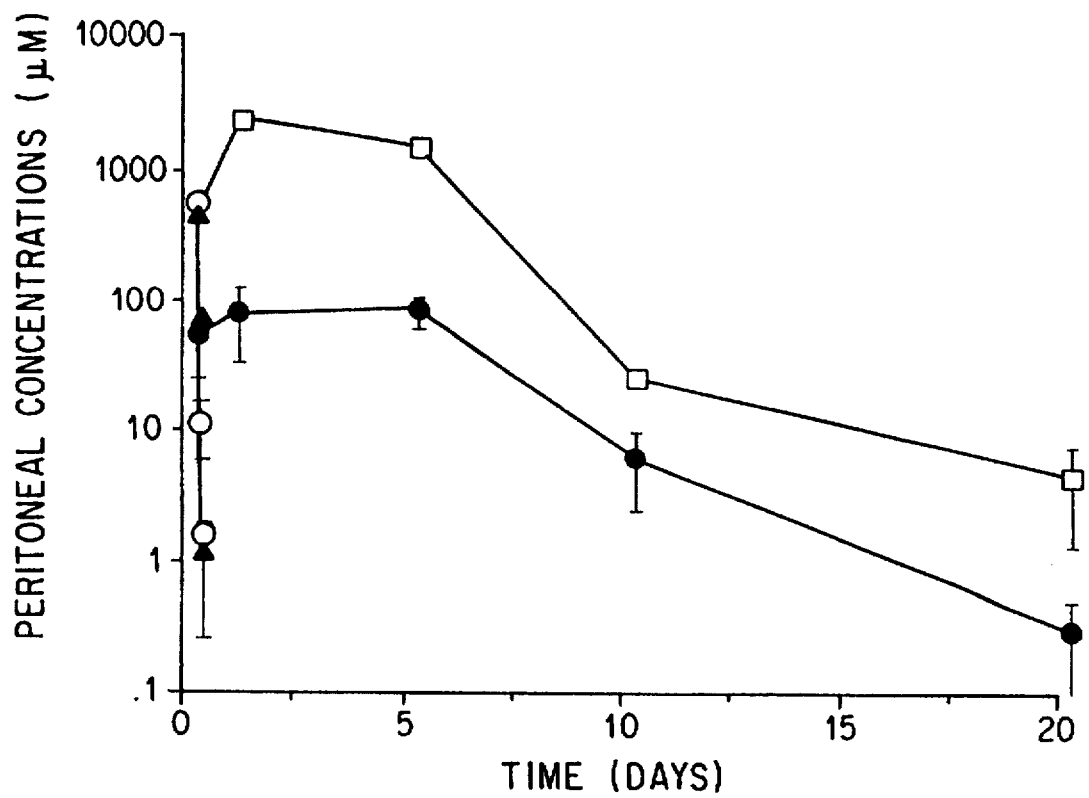
FIG. 8 shows the intraperitoneal concentrations of methotrexate after intraperitoneal injection of 10 mg/kg (22 µmoles/kg) of methotrexate as unencapsulated methotrexate (open circles), unencapsulated cyclodextrin- methotrexate complex (shaded triangles) or multivesicular liposome encapsulated methotrexate, MVL-CD-MTX (shaded circles, free; open boxes, total). Each point represents the mean and the standard deviation from a group of three mice.
Figure 9:
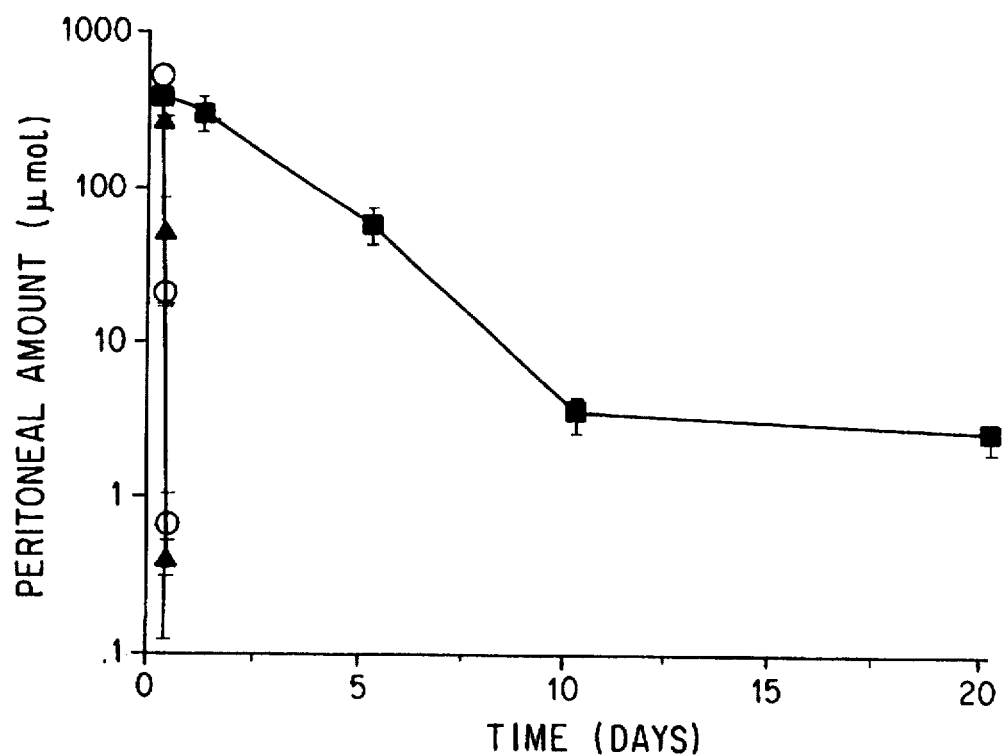
FIG. 9 shows the amounts of methotrexate remaining within the peritoneal cavity after injection of 10 mg/kg (22 µmoles/kg) of methotrexate as unencapsulated methotrexate (open circles), unencapsulated cyclodextrin- methotrexate complex (closed triangles) or multivesicular liposome encapsulated methotrexate, MVL-CD-MTX (shaded boxes). Each point represents the mean and the standard deviation from a group of three mice.

The intraperitoneal pharmacokinetics parameters are summarized in the Table 3. Following ip injection of MVL-CD-MTX, total concentration of methotrexate in the peritoneal cavity increased five-fold over the first day (FIG. 8). During this period of time, the amount of fluid in the cavity decreased significantly. After Day 1, the total concentration decreased with a half-life of 1.9 days (FIG. 9).

TABLE 3

| | Pharmacokinetic parameters of methotrexate after intraperitoneal administration | | | |
|---|---|---|---|---|
| | Unencapsulated | | MVL-CD-MTX | |
| | MTX | CD-MTX | Free | Total |
| | PERITONEAL | | | |
| Conc. $t_{1/2}$[b] (h) | 0.54 | 0.46 | 39.6 | 45.6 |
| Amount $t_{1/2}$(h) | 0.45 | 0.41 | NA[d] | 62.4 |
| $C_{max}$[c] + SD (µM) | 430 ± 13 | 379 ± 10 | 66.7 ± 18.3 | 1863 ± 168 |
| AUC (µM · h) | 233 | 316 | 12260 | 273800 |
| | PLASMA | | | |
| Conc. $t_{1/2}$(h) | 0.9 | 0.6 | 240 | NA |
| Cmax[c] + SD (µM) | 3.3 ± 0.03 | 3.3 ± 0.03 | 0.05 ± 0.05 | NA |
| AUC (µM · h) | 11.2 | 12.2 | 18.4 | NA |

[a]cyclodextrin-methotrexate
[b]half-life
[c]peak concentrations
[d]not applicable

EXAMPLE 18

Efficacy studies

Figure 10:
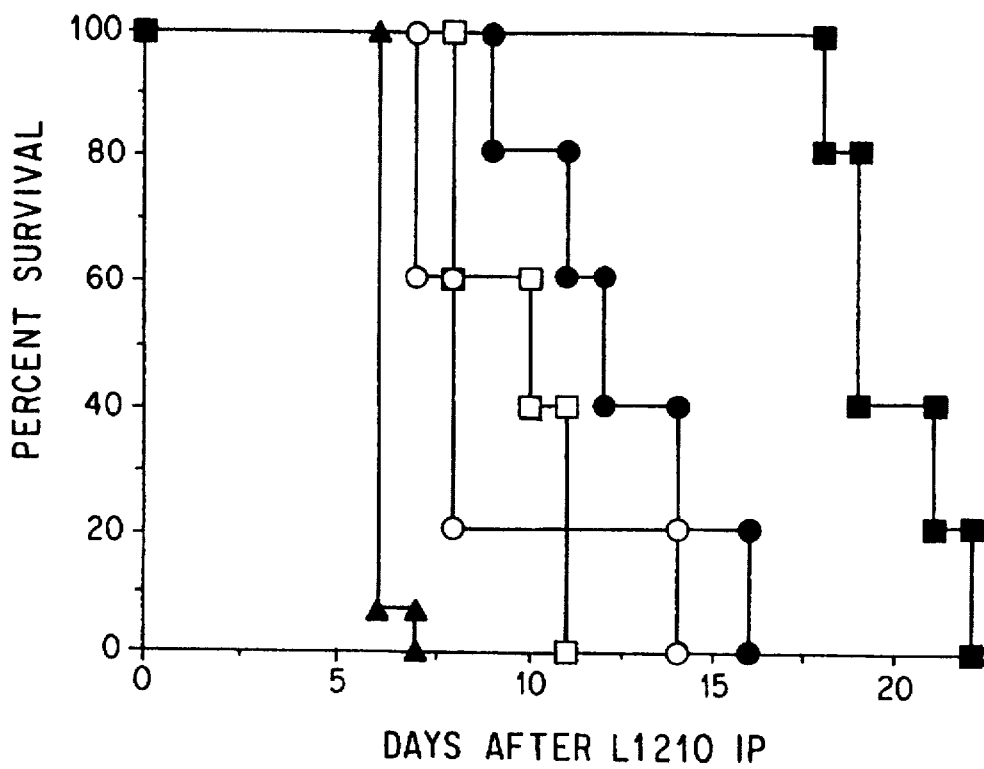
FIG. 10 shows the survival curves of mice treated intraperitoneally on day 1 with 0.9% NaCl solution (shaded triangles), 2000 mg/kg of unencapsulated methotrexate (shaded circles), 2500 mg/kg of unencapsulated methotrexate (open circles) 15 mg/kg of MVL-CD-MTX (shaded boxes) and 20 mg/kg of MVL-CD-MTX (open boxes).
Figure 5:
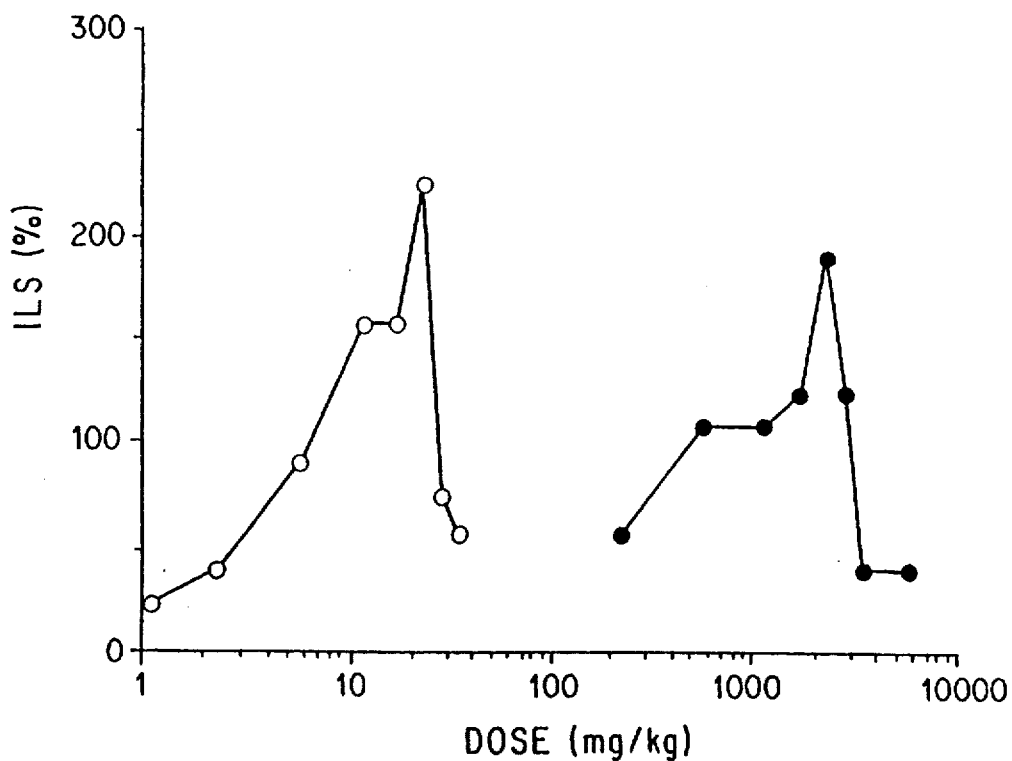
Figure 6:
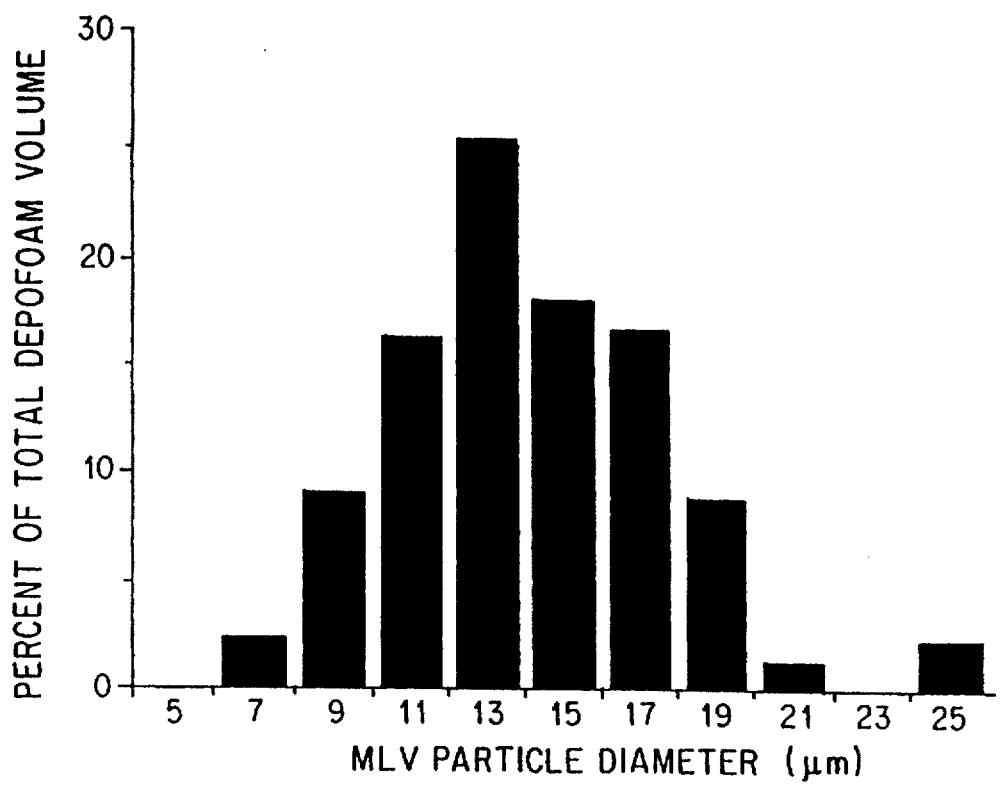
Figure 7:
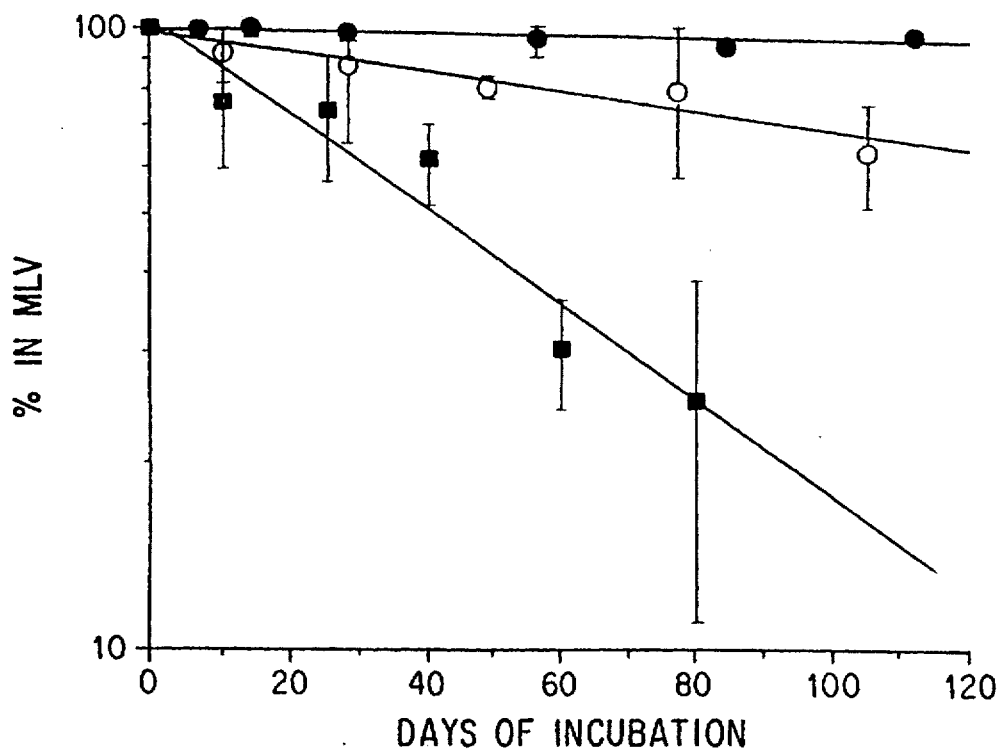
Figure 8:
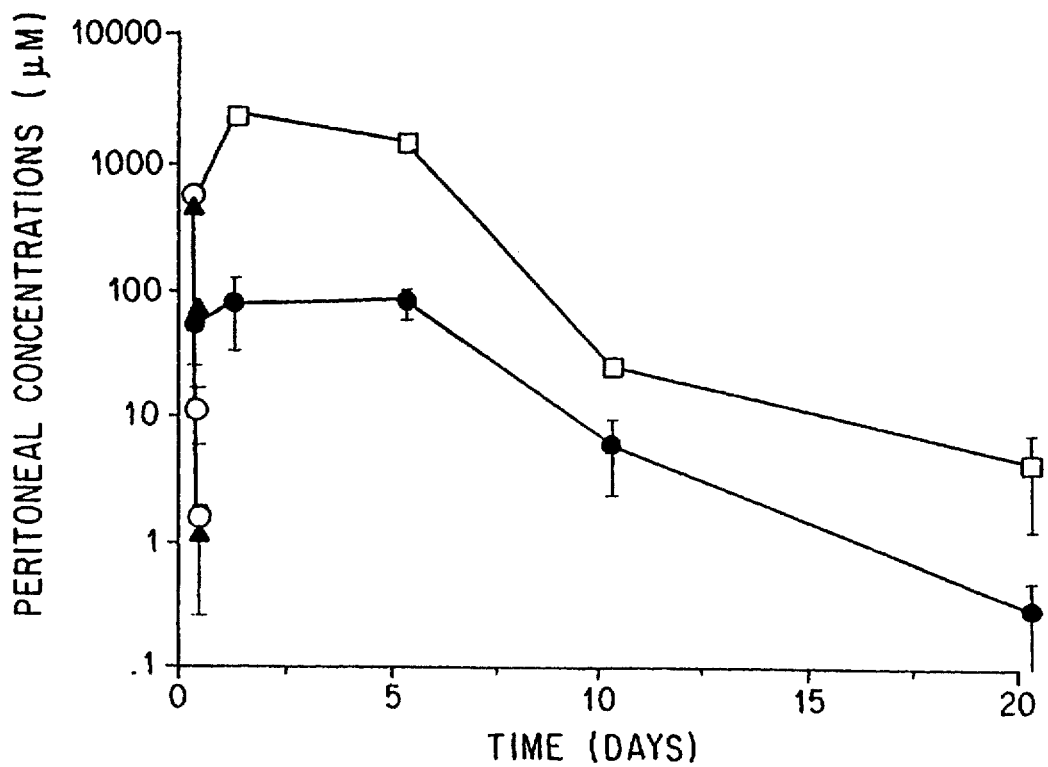
Figure 5:
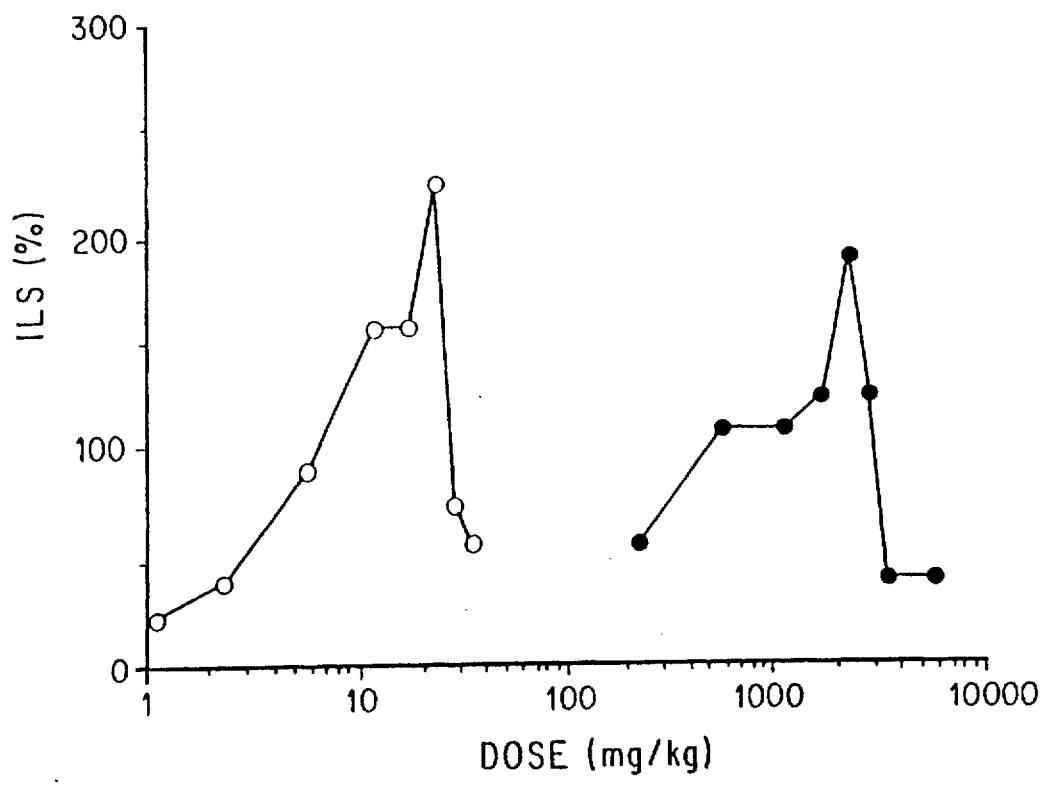
Figure 6:
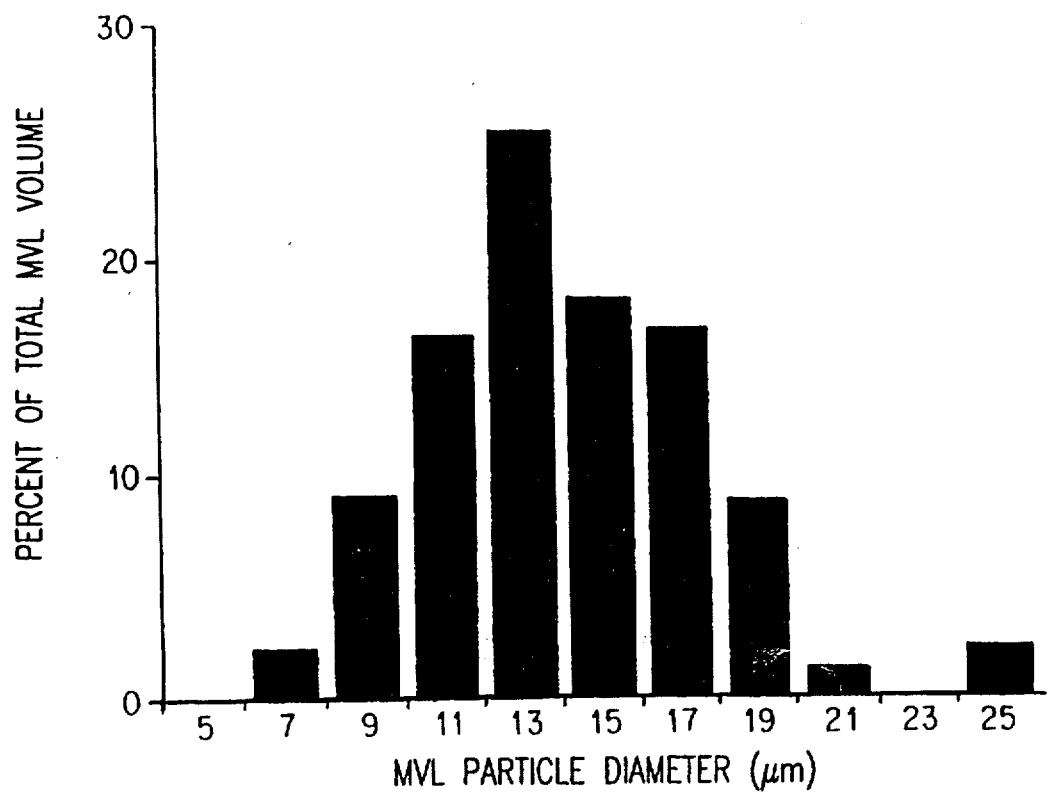
Figure 7:
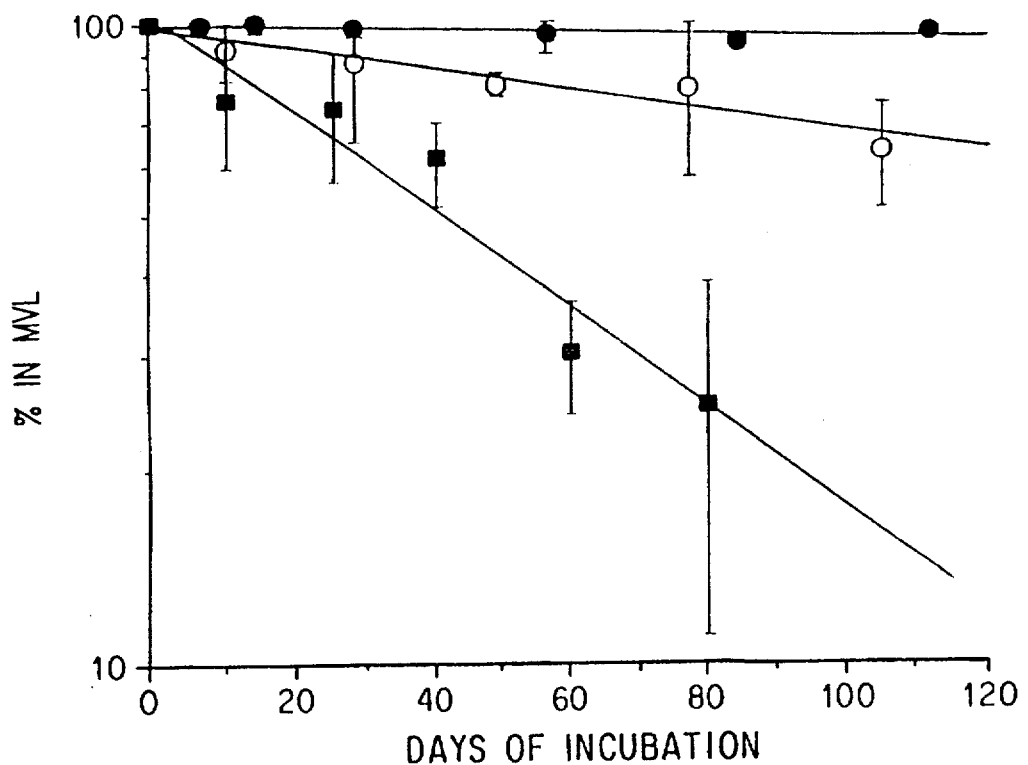
Figure 8:
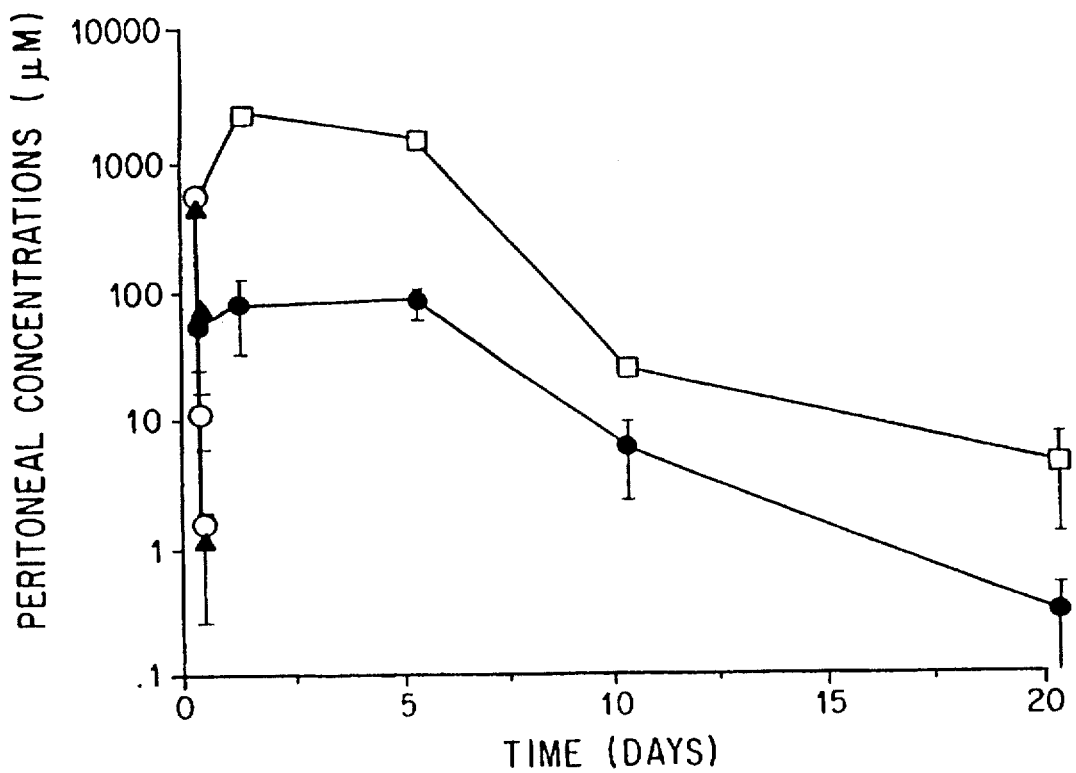

FIG. 10 shows the survival curves and FIG. 11 shows the ILS (increased life span) curves in the murine L1210 model.

The equipotent doses (EPD) appeared to be 6 mg/kg for MVL-CD-MTX and 2000 mg/kg for unencapsulated methotrexate calculated at the optimal unencapsulated methotrexate dose. Therefore, MVL-CD-MTX increased potency of single-dose methotrexate 334 fold. The maximum efficacy (ILS max) was increased from 100% ILS for unencapsulated methotrexate to 217% ILS for MVL-CD-MTX, more than 2 fold increase p<0.01 by the Mann-Whitney nonparametric test).

$LD_{50}$ was calculated after probit transformation by PHARM/PCS program (MicroComputer Specialists, Philadelphia, Pa.). $LD_{50}$ for a single dose of unencapsulated methotrexate was 2755 mg/kg and that for MVL-CD-MTX was 17.5. The therapeutic index (TI) for single IP dosage was calculated by the equation:

$$TI = LD_{50}/EPD$$

The TI for unencapsulated methotrexate was 1.4 and that for MVL-CD-MTX was 2.9. The blank multivesicular liposomes containing glucose and no methotrexate had no toxic effect on a group of five mice without tumors.

MVL-CD-MTX is quite stable in storage at 4° C. The pharmacokinetic studies showed prolonged drug exposure by encapsulation in multivesicular liposomes. The intraperitoneal half-life of free methotrexate concentration after MVL-CD-MTX administration was 73 fold (39.6 h vs. 0.54 h) longer than that after injection of unencapsulated methotrexate.

The total concentration of methotrexate in the peritoneal cavity after a MVL-CD-MTX administration actually increased during the first day and stayed above the original concentration for a period of one week. This initial increase in concentration may be due to differential clearance of the suspending medium versus the multivesicular liposome particles.

The plasma AUC after the injection of MVL-CD-MTX was similar to that after injection of unencapsulated methotrexate (18.4 and 11.2 µM/h, respectively). This indicates that all of methotrexate from MVL-CD-MTX is bioavailable to the systemic circulation.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

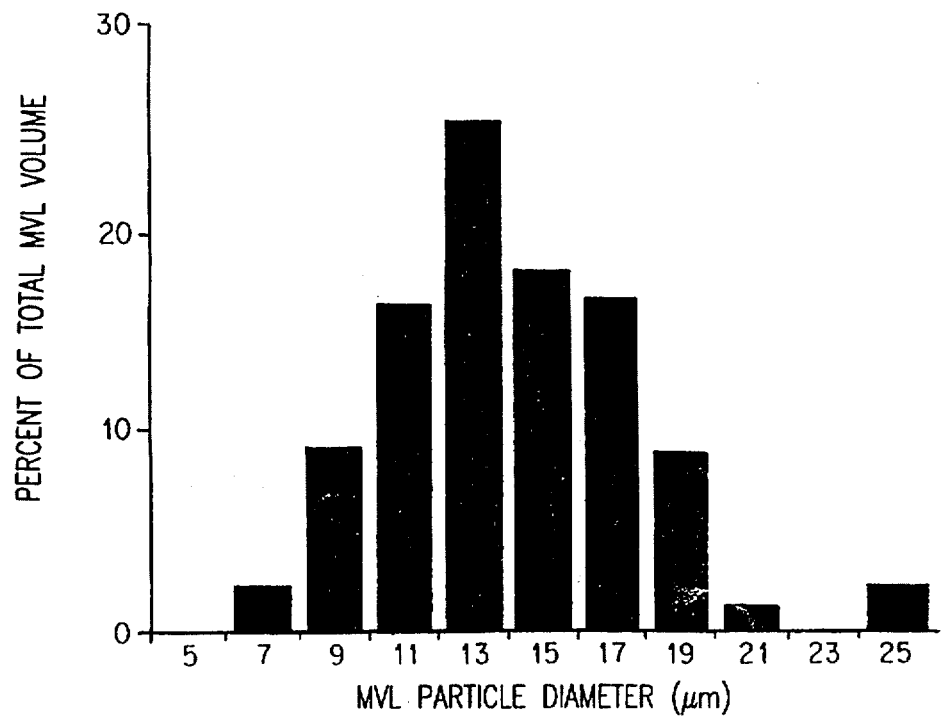

I claim:

1. A liposome comprising
   water,
   a biologically active, eater soluble compound encapsulated within the liposome, and
   a cyclodextrin in a concentration of from about 10 mg/ml to about 400 mg/ml complexed with the compound within the liposome,
   wherein the biologically active compound is released from the liopsome into an aqueous solution at about 37° C. at a slower rate than from a cyclodextrin-free liopsome, and without substantial compromise to the therapeutic index of the biologically active compound.

2. The liposome of claim 1, wherein the liposome is selected from the group of unilamellar, multilamellar and multivesicular liposomes.

3. The liposome of claim 1, wherein the water solubility of the biologically active compound is greater that 1 µg/ml in the absence of the cyclodextrin.

4. The liposome of claim 1, wherein the liposome is multivesicular.

5. The liposome of claim 1, wherein said compound is selected from the group consisting of anti-neoplastic agents, anti-infective agents, anti-depressives, antiviral agents, antinociceptive agents, anxiolytics and hormones.

6. The liposome of claim 1, wherein the compound is an anti-neoplastic agent.

7. The liposome of claim 1, wherein the compound is an anti-infective agent.

8. The liposome of claim 1, wherein the compound is an anti-viral agent.

9. The liposome of claim 1, wherein the compound is an anxiolytic.

10. The liposome of claim 1, wherein the compound is an antidepressive.

11. The liposome of claim 1, wherein the compound is a hormone.

12. The liposome of claim 1, wherein the compound is an antinociceptive agent.

13. The liposome of claim 1, wherein said cyclodextrin is selected form the group consisting of α-cyclodextrin, β-cyclodextrin, γ-cyclodextrins, methyl cyclodextrin, ethyl cyclodextrin, hydroxyethyl cyclodextrin, hydroxypropyl cyclodextrin, branched cyclodextrin, cyclodextrin polymers, and monosuccinyl dimethyl β-cyclodextrin.

14. The liposome of claim 12, wherein said cyclodextrin is 2-hydroxypropyl-β-cyclodextrin.

15. The liposome of claim 1, wherein said liposome further comprises means for targeting to a desired location within a living organism.

16. The liposme of claim 15, wherein said means is by coupling with a moiety selected from the group consisting of a sugar, a glycolipid and a protein.

17. The liposome of claim 14, wherein said protein is an antibody.

18. A method of increasing the half-life of a water soluble biologically active compound in an animal in need thereof comprising administering to the animal a liposome encapsulating the compound, wherein said liposome further encapsulates water, and a cyclodextrin in a concentration from about 10 mg/ml to about 400 mg/ml complexed with said compound; whereby the half-life of the compound is substantially increased.

19. The method of claim 18, wherein the liposome is selected from the group of unilamellar, multilamellar and multivesicular liposomes.

20. The method of claim 18, wherein water solubility of the biologically active compound is greater than 1 µg/ml in the absence of the cyclodextrin, and the cyclodextrin forms an inclusion complex with the water soluble compound.

21. The method of claim 18, wherein said cyclodextrin is selected from the group consisting of α-cyclodextrin, β-cyclodextrin, γ-cyclodextrins, methyl cyclodextrin, ethyl cyclodextrin, hydroxyethyl cyclodextrin, hydroxypropyl cyclodextrin, branched cyclodextrin, cyclodextrin polymers and monosuccinyl dimethyl β-cyclodextrin.

22. The method of claim 21, wherein said cyclodextrin is 2-hydroxypropyl-β-cyclodextrin.

23. The method of claim 18, wherein the compound is selected from the group consisting of anti-neoplastic agents, anti-infective agents, anti-depressives, antiviral agents, anti-nociceptive agents, anxiolytics and hormones.

24. The method of claim 18, wherein the compound is an anti-neoplastic agent.

25. The method of claim 18, wherein the compound is an anti-viral agent.

26. The method of claim 18, wherein the compound is an anti-infective agent.

27. The method of claim 18, wherein the compound is an anxiolytic.

28. The method of claim 18, wherein the compound is an anti-depressive agent.

29. The method of claim 18, wherein the compound is a hormone.

30. The method of claim 18, wherein compound is an anti-nociceptive agent.

31. The method of claim 18, wherein the cyclodextrin is selected from the group consisting of α-cyclodextrin, β-cyclodextrin, γ-cyclodextrins, methyl cyclodextrin, ethyl cyclodextrin, hydroxyethyl cyclodextrin, hydroxypropyl cyclodextrin, branched cyclodextrin, cyclodextrin polymers and monosuccinyl dimethyl β-cyclodextrin.

32. The method of claim 31, wherein the cyclodextrin is 2-hydroxypropyl-β-cyclodextrin.

33. A method of treating a pathophysiological state in an individual in need thereof comprising administering a liposome to the individual, said liposome comprising a therapeutically effective amount of a water soluble, biologically active compound complexed with a cyclodextrin, wherein the concentration of the cyclodextrin is from about 10 mg/ml to about 400 mg/ml, and the biologically active substance and the cyclodextrin are encapsulated within the liposome; whereby the half-life of the compound in the individual is substantially increased.

34. The liposome of claim 3, wherein the compound forms an inclusion complex with the cyclodextrin.

35. The method of claim 20, wherein the compound forms an inclusion complex with the cyclodextrin.

36. The method of claim 22 wherein the liposome is a multivesicular liposome, the compound is methotrexate, and the half-life of the compound is increased from about 18 to about 206-fold over that of a unencapsulated form of the compound.

37. The method of claim 33, wherein said liposome is selected from the group of unilamellar, multilamellar and multivesicular liposomes.

38. The method of claim 33, wherein the water solubility of the compound is greater than 1 μg/ml in the absence of the cyclodextrin, and the cyclodextrin forms an inclusion complex with the water soluble compound.

39. The method of claim 33, wherein the compound is selected from the group consisting of anti-neoplastic agents, anti-infective agents, anti-depressives, antiviral agents, anti-nociceptive agents, anxiolytics and hormones.

40. The method of claim 33, wherein the compound is an anti-neoplastic agent.

41. The method of claim 33, wherein the compound is an anti-viral agent.

42. The method of claim 33, wherein the compound is an anti-infective agent.

43. The method of claim 33, wherein the compound is an anxiolytic agent.

44. The method of claim 33, wherein the compound is an anti-depressive agent.

45. The method of claim 33, wherein the compound is an hormone.

46. The method of claim 33, wherein the compound is an anti-nociceptive agent.

47. The method of claim 33, wherein said cyclodextrin is selected from the group consisting of α-cyclodextrin, β-cyclodextrin, γ-cyclodextrins, methyl cyclodextrin, ethyl cyclodextrin, hydroxyethyl cyclodextrin, hydroxypropyl cyclodextrin, branched cyclodextrin, cyclodextrin polymers and monosuccinyl dimethyl β-cyclodextrin.

48. The method of claim 47, wherein said cyclodextrin is 2-hydroxypropyl-β-cyclodextrin.

* * * * *

UNITED STATES PATENT AND TRADEMARK OFFICE
CERTIFICATE OF CORRECTION

PATENT NO.    : 5,759,573

DATED         : June 2, 1998

INVENTOR(S)   : Sinil Kim

It is certified that error appears in the above-identified patent and that said Letters Patent is hereby corrected as shown below:

The Title page should be deleted and substitute therefor the attached Title page.

Figure 6:
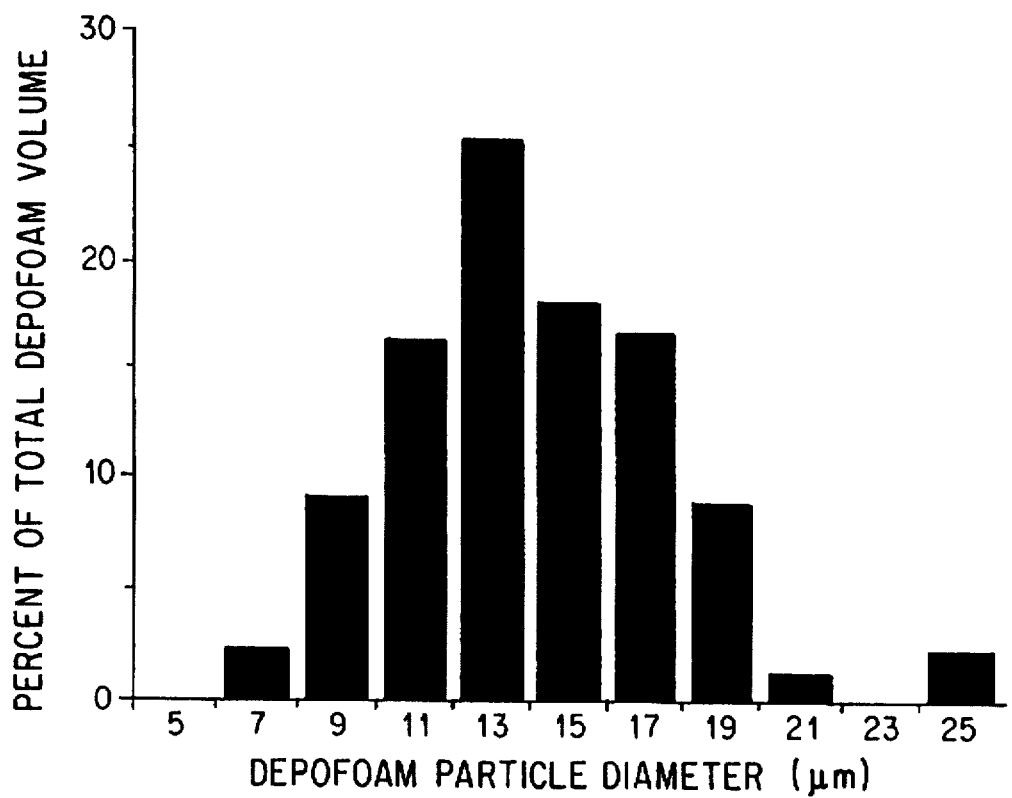
FIG. 6 shows the volume-adjusted size distribution of the multivesicular liposome formulation of methotrexate, MVL-CD-MTX. Diameters of particles were measured in groups of 2-µm intervals from a photomicrograph. The number of particles in each size group was multiplied by the cube of the radius to obtain relative volumes of each size category and then divided by the sum of the relative volumes of all particles to obtain percent of total volume represented by each size category. The capture volume was 12.9±1.0 µl/µmole of lipids.

Drawings:

Delete Fig 6, and substitute therefor Fig 6, as shown on the attached sheet.

Figure 7:
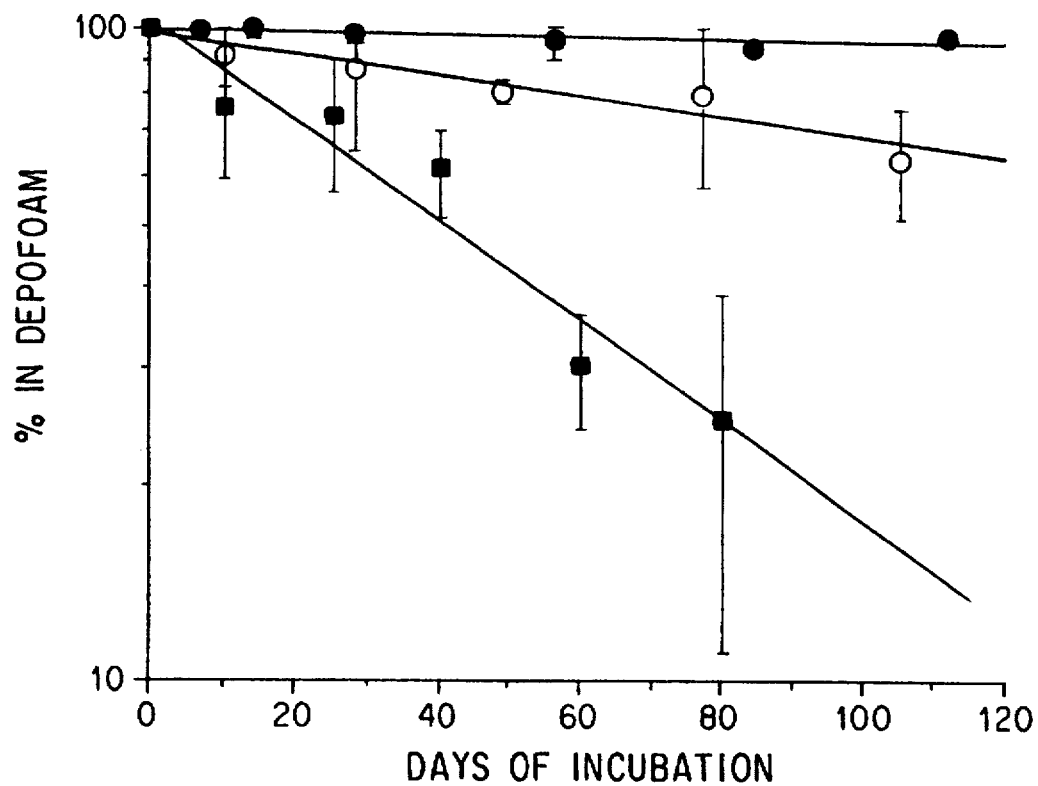
FIG. 7 shows the release of methotrexate from MVL-CD-MTX suspended in 0.9% NaCl solution kept at 4° C. (shaded circle); in 0.9% NaCl solution at 37° C. (open circle); and in human plasma at 37° C. (shaded box). Each point is the mean and the standard deviation from three experiments. The ordinate scale is logarithmic.

Delete Fig 7, and substitute therefor Fig 7, as shown on the attached sheet.

United States Patent [19]
Kim

[11] Patent Number: 5,759,573
[45] Date of Patent: Jun. 2, 1998

[54] CYCLODEXTRIN LIPOSOMES ENCAPSULATING PHARMACOLOGIC COMPOUNDS AND METHODS FOR THEIR USE

[75] Inventor: Sinil Kim, Solana Beach, Calif.

[73] Assignee: DepoTech Corporation, San Diego, Calif.

[21] Appl. No.: 535,256

[22] PCT Filed: Apr. 22, 1994

[86] PCT No.: PCT/US94/04490

§ 371 Date: Dec. 21, 1995

§ 102(e) Date: Dec. 21, 1995

[87] PCT Pub. No.: WO94/23697

PCT Pub. Date: Oct. 27, 1994

[51] Int. Cl.$^6$ .................... A61K 9/127; A61K 9/133
[52] U.S. Cl. ........................ 424/450; 436/829
[58] Field of Search .................. 424/450, 1.21, 424/9.321, 9.51; 428/402.2; 436/829; 514/58

[56] References Cited

U.S. PATENT DOCUMENTS 4,935,407 6/1990 Luider ........................... 514/58
5,236,907 8/1993 Ueno ............................ 514/530

OTHER PUBLICATIONS

Takada BBA 802, 237, 1984.

Osrro Liposomes Marcel Dekker Inc p. 277, 1987.

Manosroi Drug Dev. & Ind. Pharmacy 16(5) p. 37 (1990).

*Primary Examiner*—Gollamudi S. Kishore
*Attorney, Agent, or Firm*—Fish & Richardson P.C.

[57] ABSTRACT

Liposomes containing cyclodextrin in the encapsulated aqueous phase are useful for encapsulation of biologically active substances, especially those which are hydrophilic. The encapsulated cyclodextrin facilitates a slow, controlled release of pharmacologic compounds from the liposomes. The novel methods of the present invention allow the treatment of a variety of pathophysiological states by administering the cyclodextrin-containing liposomes encapsulating the pharmacologic compounds. The present invention also provides a novel method of extending the half life of a pharmacologic compound in an animal.

48 Claims, 6 Drawing Sheets

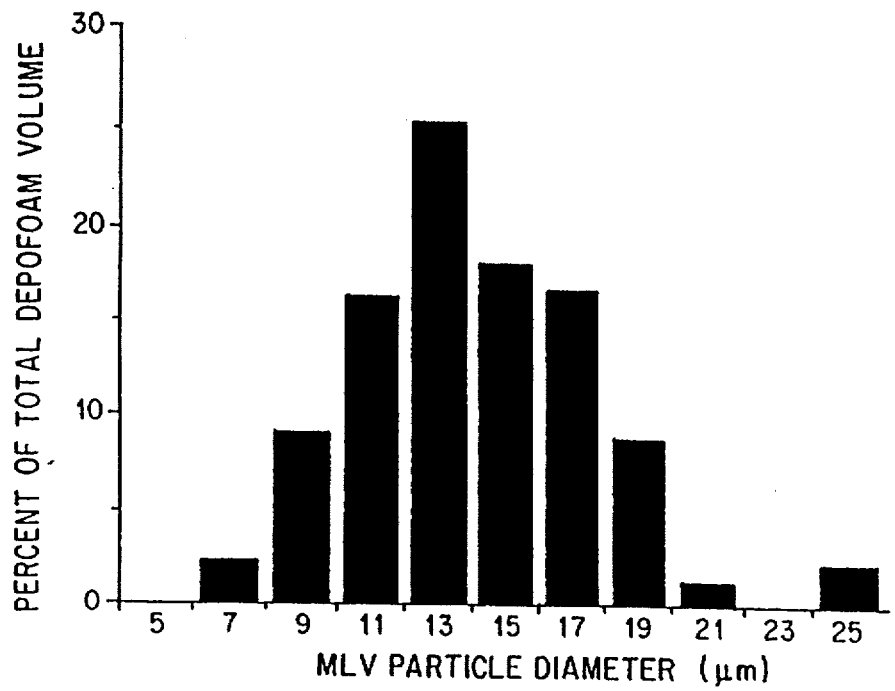

UNITED STATES PATENT AND TRADEMARK OFFICE
CERTIFICATE OF CORRECTION

PATENT NO. : 5,759,573

DATED : 6/2/98

INVENTOR(S) : DepoTech Corporation

It is certified that error appears in the above-identified patent and that said Letters Patent is hereby corrected as shown below:

| | |
|---|---|
| Fig. 6 | change "DEPOFOAM" to "MVL" in both the X and Y axes. |
| Fig. 7 | change "DEPOFOAM" to "MVL" in Y axis. |
| Col. 1, line 51 | change "substituted" to "substances are well suited". |
| Col. 3, line 8 | delete "multivesicular liposomes encapusulating methotrexate and cyclodextrin" and substitute "methotrexate coencapsulated with cyclodextrin in multivesicular liposomes". |
| Col.3, line 18 | delete "closed square cranial". |
| Col. 3, line 29 | change "(open circles)" to "(closed circles)". |
| Col. 3, line 30 | change "(closed circles)" to "(open circles)". |
| Col. 4, line 3 | change "time" to "span". |
| Col. 5, line 21 | delete "oil" and substitute "of". |
| Col. 6, line 59 | "a" should read --aqueous internal--. |
| Col. 12, line 23 | delete "methotrecate oar" and substitute "methotrexate or". |
| Col.. 12, line 30 | delete "ILS-(T/C)/C x100%" and substitute "ILS=(T/C)x100". |
| Co.l. 13, line 20 | change "40 x volumes" to "40 volumes". |
| Col. 13, line 42 | delete "2-hydroxypropyll-β-cyclodextrin" and susbstitute "2-hydroxypropyl-β-cyclodextrin". |
| Col. 14, line 21 | delete "11.3 ± μM" and substitute "14.1 ± 3.4 μM". |
| Col. 14, line 22 | delete "(FIG. 6 and 7)" and substitute "(FIG. 6)". |
| Col. 14, line 28 | delete "(FIG. 8)" and susbstitute "(FIG. 7)". |

UNITED STATES PATENT AND TRADEMARK OFFICE
CERTIFICATE OF CORRECTION

PATENT NO.      : 5,759,573

DATED           : 6/2/98

INVENTOR(S)     : DepoTech Corporation

It is certified that error appears in the above-identified patent and that said Letters Patent is hereby corrected as shown below:

Col. 14, line 37    delete "concentration" and substitute "amount".

Col. 15, line 61    replace "eater" with "water".

Col. 15, line 67    delete "liopsome" and substitute "liposome".

Signed and Sealed this

Twenty-second Day of December, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,759,573
DATED : June 2, 1998
INVENTOR(S) : Sinil Kim

It is certified that error appears in the above-identified patent and that said Letters Patent is hereby corrected as shown below:

The title page, should be deleted to appear as per attached title page.

Please delete drawing sheets 3 of 6 and 4 of 6, and substitute the same as per attached.

Signed and Sealed this

Seventh Day of September, 1999

Attest:

Q. TODD DICKINSON

Attesting Officer

Acting Commissioner of Patents and Trademarks

United States Patent [19]

Kim

[11] Patent Number: 5,759,573
[45] Date of Patent: Jun. 2, 1998

[54] CYCLODEXTRIN LIPOSOMES ENCAPSULATING PHARMACOLOGIC COMPOUNDS AND METHODS FOR THEIR USE

[75] Inventor: Sinil Kim, Solana Beach, Calif.

[73] Assignee: DepoTech Corporation, San Diego, Calif.

[21] Appl. No.: 535,256

[22] PCT Filed: Apr. 22, 1994

[86] PCT No.: PCT/US94/04490

§ 371 Date: Dec. 21, 1995

§ 102(e) Date: Dec. 21, 1995

[87] PCT Pub. No.: WO94/23697

PCT Pub. Date: Oct. 27, 1994

[51] Int. Cl.$^6$ ............................ A61K 9/127; A61K 9/133
[52] U.S. Cl. ............................................ 424/450; 436/829
[58] Field of Search ........................... 424/450, 1.21, 424/9.321, 9.51; 428/402.2; 436/829; 514/58

[56] References Cited

U.S. PATENT DOCUMENTS 4,935,407  6/1990  Luider ............................... 514/58
5,236,907  8/1993  Ueno ................................ 514/530

OTHER PUBLICATIONS

Takada BBA 802, 237, 1984.

Osrro Liposomes Marcel Dekker Inc p. 277, 1987.

Manosroi Drug Dev. & Ind. Pharmacy 16(5) p. 37 (1990).

Primary Examiner—Gollamudi S. Kishore
Attorney, Agent, or Firm—Fish & Richardson P.C.

[57] ABSTRACT

Liposomes containing cyclodextrin in the encapsulated aqueous phase are useful for encapsulation of biologically active substances, especially those which are hydrophilic. The encapsulated cyclodextrin facilitates a slow, controlled release of pharmacologic compounds from the liposomes. The novel methods of the present invention allow the treatment of a variety of pathophysiological states by administering the cyclodextrin-containing liposomes encapsulating the pharmacologic compounds. The present invention also provides a novel method of extending the half life of a pharmacologic compound in an animal.

48 Claims, 6 Drawing Sheets